United States Patent
Hirst et al.

(10) Patent No.: US 11,697,796 B2
(45) Date of Patent: Jul. 11, 2023

(54) MEDIA AND METHODS FOR ENHANCING THE SURVIVAL AND PROLIFERATION OF STEM CELLS

(71) Applicant: STEMCELL Technologies Canada Inc., Vancouver (CA)

(72) Inventors: Adam Hirst, Vancouver (CA); Arwen Hunter, Vancouver (CA); Melanie Kardel, Vancouver (CA); Wing Chang, Vancouver (CA)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 498 days.

(21) Appl. No.: 16/480,025

(22) PCT Filed: Jan. 23, 2018

(86) PCT No.: PCT/CA2018/050076
§ 371 (c)(1),
(2) Date: Jul. 23, 2019

(87) PCT Pub. No.: WO2018/132926
PCT Pub. Date: Jul. 26, 2018

(65) Prior Publication Data
US 2020/0017825 A1 Jan. 16, 2020

Related U.S. Application Data

(60) Provisional application No. 62/608,875, filed on Dec. 21, 2017, provisional application No. 62/518,776, filed on Jun. 13, 2017, provisional application No. 62/449,413, filed on Jan. 23, 2017.

(51) Int. Cl.
*C12N 5/0735* (2010.01)
*C12N 5/074* (2010.01)

(52) U.S. Cl.
CPC .......... *C12N 5/0606* (2013.01); *C12N 5/0696* (2013.01); *C12N 2500/36* (2013.01); *C12N 2501/115* (2013.01); *C12N 2501/15* (2013.01); *C12N 2501/727* (2013.01); *C12N 2501/999* (2013.01); *C12N 2533/90* (2013.01)

(58) Field of Classification Search
CPC ................................................ C12N 2500/36
See application file for complete search history.

(56) References Cited

U.S. PATENT DOCUMENTS

| 9,399,761 B2 | 7/2016 | Angel et al. |
| 2010/0279412 A1 | 11/2010 | Kato et al. |
| 2012/0279412 A1 | 11/2012 | Hash et al. |
| 2013/0309768 A1 | 11/2013 | Furue et al. |

FOREIGN PATENT DOCUMENTS

| CA | 2782296 A1 | 6/2011 | |
| CA | 2981277 A1 * | 10/2016 | ........... C12N 5/0623 |
| CA | 2981277 A1 | 10/2016 | |
| CN | 101052712 A | 10/2007 | |
| CN | 101182464 A | 5/2008 | |
| CN | 105283541 A | 1/2016 | |
| JP | 2009542247 A | 12/2009 | |
| JP | 2012175962 A | 9/2012 | |
| WO | WO2008/007082 A2 | 1/2008 | |
| WO | 2015/042356 A1 | 3/2015 | |
| WO | WO-2016159179 A1 * | 10/2016 | ........... C12N 5/0623 |

OTHER PUBLICATIONS

Machine Translation of WO 2016/159179 A1 (Year: 2016).*
Four page printout from Encyclopedia Britannica Online (Year: 2021).*
Palomer et al., 2018, Trends in Endocrinology & Metabolism, vol. 29(3), pp. 178-190 (Year: 2018).*
Abdelmagid et al., 2015, PLOS One, vol. 10(2), pp. 1-16 (Year: 2015).*
Chu et al., 2011, Scandinavian J. Immunol., vol. 73, pp. 508-511 (Year: 2011).*
Govardhanagiri et al., 2019, Chapter 8—Small Molecules and Pancreatic Cancer Trials and Troubles, pp. 117-131, 1 page printout only—abstract. (Year: 2019).*
Horiguchi, et al. "Serum Replacement with Albumin-Associated Lipids Prevents Excess Aggregation and Enhances Growth of Induced Pluripotent Stem Cells in Suspension Culture", Biotechnol Prog., Jul. 8, 2016, vol. 32, No. 4, pp. 1009-1016.
AlbuMAX I Lipid-Rich BSA [online]. Thermo Fisher Scientific. Publication date unknown [retrieved on Apr. 27, 2018] from <http://www.thermofisher.com/order/catalog/product/11020021>.

(Continued)

*Primary Examiner* — Anoop K Singh
*Assistant Examiner* — David A Montanari
(74) *Attorney, Agent, or Firm* — Bereskin & Parr LLP/S.E.N.C.R.L., s.r.l.; Micheline Gravelle

(57) ABSTRACT

The present disclosure relates to improved supplements, culture media and methods for enhancing the survival or proliferation of mammalian stem cells. In particular, adding a lipid supplement, such as a lipid-enriched carrier (e.g. a lipid-enriched albumin), to the culture medium may enhance the survival and/or proliferation of the stem cells by at least 5% to 65% as compared to a culture medium that does not contain the lipid supplement.

12 Claims, 14 Drawing Sheets

(56) References Cited

OTHER PUBLICATIONS

Eynard, AR et al., Eicosatrienoic acid (20:3 n-9) inhibits the expression of E-cadherin and desmoglein in human squamous cell carcinoma in vitro. Prostaglandins Leukot Essent Fatty Acids. Dec. 1998, vol. 59, p. 371-377.
Furue, MK et al., Heparin promotes the growth of human embryonic stem cells in a defined serum-free medium. ProcNatl Acad Sci USA. Sep. 9, 2008, vol. 105, p. 13409-13414.
Garcia-Gonzalo, FR et al. Albumin-associated lipids regulate human embryonic stem cell self-renewal. PLoS One. Jan. 2, 2008, vol. 3, p. e1384.
Gauthaman, K. et al., Effect of ROCK inhibitor Y-27632 on normal and variant human embryonic stem cells (hESCs) in vitro: its benefits in hESC expansion. Stem Cell Rev. Mar. 2010, vol. 6, p. 86-95.
Suzuki, C. et al., Lipid-rich bovine serum albumin improves the viability and hatching ability of porcine blastocysts products in vitro. J Reprod Dev. 2016, vol. 62, p. 79-86.
Hui Zhang et al., "Distinct Metabolic States Can Support Self-Renewal and Lipogenesis in Human Pluripotent Stem Cells Under Different Culture Conditions". Cell Reports, vol. 16, No. 6, p. 1536-1547, Aug. 1, 2016.
Kitajima, et al. "Clonal Expansion of Human Pluripotent Stem Cells on Gelatin-Coated Surface", Biochemical and Biophysical Research Communications, 396 (Apr. 15, 2010) p. 933-938.

\* cited by examiner

MEDIA AND METHODS FOR ENHANCING THE SURVIVAL AND PROLIFERATION OF STEM CELLS

RELATED APPLICATION

This application is a national phase entry application of Patent Cooperation Treaty Application No. PCT/CA2018/050076, filed Jan. 23, 2018 (which designates the U.S.), which claims the benefit under 35 USC §119(e) from United States Provisional Application Nos. 62/449,413, filed on Jan. 23, 2017 (now abandoned), 62/518,776, filed on Jun. 13, 2017 (now abandoned) and 62/608,875, filed on Dec. 21, 2017 (now abandoned), all of which are incorporated herein by reference in their entirety.

BACKGROUND

Stem cell research has become a fast moving research field with a wide variety of potential applications ranging from the study of embryonic development, disease modelling, toxicology screening, and cell based therapies. Since the derivation of the first human embryonic stem cell lines (ESCs), ESCs have received wide public attention owing to their potential use in regenerative medicine (Thomson et al. 1998). The seemingly indefinite proliferative capability of ESCs coupled with their ability to differentiate into all somatic cell types makes them an attractive renewable resource of transplantable human tissue.

Furthermore, since the discovery that differentiated somatic cells could be reprogrammed to an ESC-like state by transfecting cells with stem cell transcription factors, the potential for personalised medicine was realised (Takahashi and Yamanaka 2006). Patient-specific somatic cells may be induced to pluripotent stem cell (iPSC) lines, and transplanted back into the patient in order to decrease the risk of immune-rejection following transplantation.

As with any fast moving research area, methods for generating iPSCs have become more efficient. Furthermore, with the emergence of non-integrating technologies, iPSCs have become more clinically relevant (Maeder and Gersbach 2016). Such advances coupled with the recent development of more accessible gene editing techniques (ZFNs, TALENs, CRISPR etc.) may pave the way to remedy disease-specific mutations prior to transplanting cells back into the patient.

Gene-editing is also a fast moving research field with new applications and modifications being published frequently. The unpredictable nature of cellular DNA-repair mechanisms following gene-editing, which in most instances causes double strand breaks at specific places in the genome, can lead to a population of target cells comprising different indels. This is a potential problem when trying to assess what effect the altered genome has on the cells when different mutations could display different phenotypes. To resolve this issue a homogeneous population containing the same alteration can be obtained by clonal derivation of new cell lines from a single cell.

The efficiency of deriving cell lines from single cells can be very challenging, human pluripotent stem cells are one example where cloning efficiency can be very low.

Human pluripotent stem cells, unlike their murine counterparts, are difficult to culture as single cells, seeding single cells at low to clonal densities can result in mass cell death shortly after plating. This has been attributed to certain bottlenecks following single cell seeding; of the cells that do survive the initial plating, many of which do not re-enter the cell cycle, and of those cells that do re-enter the cell cycle many of the daughter cells do not survive, and very few form long-term proliferating colonies (Barbaric et al. 2014).

Approaches to solving the foregoing problems associated with the culture of single mammalian stem cells have involved complex media formulations comprising an array of small molecule inhibitors. Such media formulations are inadequate, on account of the cost of manufacture and their inefficiency. Accordingly, there remains a need for culture media and methods to enhance the survival and/or proliferation of mammalian stem cells in in vitro cultures.

SUMMARY

The present disclosure relates to improved supplements, culture media and methods for enhancing the survival or proliferation of mammalian stem cells. In particular, the inventors have shown that adding a lipid supplement, such as a lipid-enriched carrier (e.g. a lipid-enriched albumin), to the culture medium may enhance the survival and/or proliferation of the stem cells by at least 5% to 65% as compared to a culture medium that does not contain the lipid supplement. More particularly, adding a lipid supplement, such as a lipid-enriched carrier (e.g. a lipid-enriched albumin), to the culture medium may enhance the survival and/or proliferation of the stem cells by approximately 10% to 40%. An average cloning efficiency using the described lipid supplement and/or culture medium is approximately 30%.

In one aspect of this disclosure a lipid supplement for enhancing the survival or proliferation of one or more mammalian stem cells is provided. In one embodiment, the lipid supplement may comprise one or more lipids. In another embodiment, the lipid supplement may comprise one or more lipids in the presence of a carrier. In a further embodiment, the lipid supplement may comprise a lipid-enriched carrier, such as a lipid-enriched albumin.

In another aspect of this disclosure a culture medium for enhancing the survival or proliferation of one or more mammalian stem cells is provided. In one embodiment the culture medium may comprise a lipid supplement. In one embodiment, the lipid supplement may comprise one or more lipids. In another embodiment, the lipid supplement may comprise one or more lipids in the presence of a carrier. In a further embodiment, the lipid supplement of the culture medium for enhancing the survival or proliferation of one or more mammalian stem cells may comprise a lipid-enriched carrier, such as a lipid-enriched albumin.

In one embodiment, the culture medium comprises a lipid supplement, such as a lipid-enriched albumin, and one or more survival factors such as one or more small molecule inhibitors.

In another aspect, the culture medium may comprise an extracellular matrix. In embodiments where the culture medium comprises an extracellular matrix, a concentration of the extracellular matrix may be below a gelation threshold thereof. In one embodiment, the extracellular matrix comprises one or more monomatrix components. Such culture media may enhance the survival and/or proliferation (ie. enhance cloning efficiency, increase the number of recovered clones, and/or increase the survival rate) of the one or more stem cells by about 5% to about 65%.

In another embodiment, the culture medium comprising an extracellular matrix, may optionally further comprise a lipid supplement.

In another embodiment of a culture medium for enhancing the survival or proliferation of one or more mammalian stem cells comprising an extracellular matrix, the culture medium may still further comprise one or more survival factors.

In another embodiment, the present disclosure provides a lipid supplement-free culture medium for enhancing the survival or proliferation of one or more mammalian stem cells wherein the media comprises an extracellular matrix.

In one embodiment, a concentration of the extracellular matrix is below a gelation threshold thereof. In some embodiments the extracellular matrix comprises one or more monomatrix components.

In another embodiment, the lipid supplement-free culture medium comprises one or more survival factors such as one or more small molecule inhibitors.

In another aspect, the present disclosure provides methods of enhancing the survival or proliferation of mammalian stem cells comprising culturing the stem cells in a culture medium comprising a lipid-enriched albumin.

In one embodiment, the culture media may comprise an extracellular matrix. In another embodiment, a concentration of the extracellular matrix may be below a gelation threshold thereof.

In one embodiment, culturing comprises culturing the one or more mammalian stem cells as a monolayer. In another embodiment, culturing comprises culturing the one or more mammalian stem cells under non-adherent conditions In a further aspect, the present disclosure provides methods of enhancing the survival or proliferation of one or more mammalian stem cells. In one embodiment, the method may comprise culturing the one or more mammalian stem cells in the presence of a lipid supplement, as described herein. In another embodiment, the method may comprise culturing the one or more mammalian stem cells in the presence of a culture medium, as described herein. In a further embodiment, the method may comprise culturing the stem cells in a lipid supplement-free culture medium comprising an extracellular matrix.

In one embodiment, a concentration of the extracellular matrix may be below a gelation threshold thereof.

In one embodiment, culturing comprises culturing the one or more mammalian stem cells as a monolayer. In another embodiment, culturing comprises culturing the one or more mammalian stem cells under non-adherent conditions.

In one embodiment, the method for enhancing the survival or proliferation of one or more mammalian stem cells may comprise:
  a) providing one or mammalian stem cells;
  b) culturing the one or more mammalian stem cells in a culture medium comprising a lipid supplement;
  c) enhancing the survival or proliferation of the one or more mammalian stem cells; and
  d) yielding a 5%-65% cloning efficiency.

In another embodiment, the method for enhancing the survival or proliferation of one or more mammalian stem cells may comprise:
  a) providing one or mammalian stem cells;
  b) culturing the one or more mammalian stem cells in a culture medium comprising an extracellular matrix below a gelation threshold thereof, and optionally a lipid supplement;
  c) enhancing the survival or proliferation of the one or more mammalian stem cells; and
  d) yielding a 5%-65% cloning efficiency.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 10 is a bar graph showing that lipids do not need to be lipid-loaded by can be added in the presence of a carrier to increase cloning efficiency of hPSCs in a protein rich medium (A) and a protein free medium (B).

DETAILED DESCRIPTION

Figure 1:
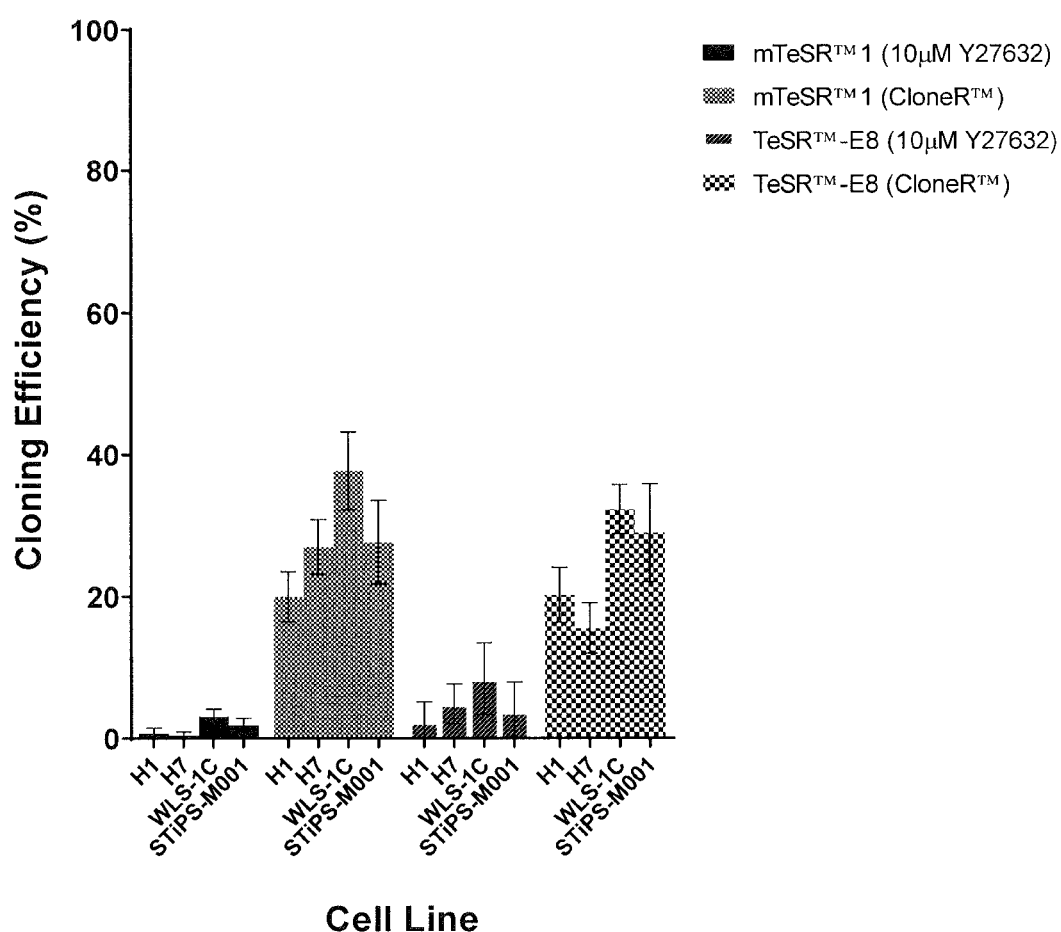
FIG. 1 is a bar graph showing the % cloning efficiency for various cell lines cultured in different culture media.

This disclosure relates to methods and media for enhancing the survival or proliferation of mammalian stem cells.

Where used herein, "enhancing the survival or proliferation" means increased survival or proliferation of one or more cells when cultured in the presence of a lipid supplement or an extracellular matrix, or both, in comparison to one or more cells not cultured in the presence of the lipid supplement or the extracellular matrix, or both, but otherwise cultured under the same or substantially the same conditions.

Where used herein, "lipid supplement" means a preparation of one or more lipids and/or lipid-like substances. The preparation may be provided as free one or more lipids (or free one or more fatty acids) and/or lipid-like substances. Or, the preparation may be provided in the presence of a carrier. Or, the preparation may be loaded on a carrier, forming a lipid-enriched carrier. By way of non-limiting example, the lipid-enriched carrier may be a lipid-enriched albumin. The preparation of one or more lipids and/or lipid-like substances may be loaded onto a carrier prior to exposing a cell culture of one or more mammalian stem cells thereto. Or, the preparation of one or more lipids and/or lipid-like substances may be combined with a carrier prior to exposing a cell culture of one or more mammalian stem cells thereto. Or, the preparation of one or more lipids and/or lipid-like substances and a carrier may be separately provided to a cell culture of one or more mammalian stem cells. In any embodiment the lipid supplement may be provided to cell culture in a cell culture medium, such as a stem cell culture medium.

Where used herein, "carrier" means a biological or non-biological agent, substance, composition or complex that is capable of transporting some or all of the lipid supplement to a cell, whether in vitro or in vivo. More specifically, the carrier is capable of transporting one or more lipids to a cell, whether in vitro or in vivo. By way of non-limiting examples, a carrier may be an albumin, a micelle, a liposome, an extracellular vesicle, an exosome, a cyclodextrin, a nanostructured lipid carrier, or otherwise.

Where used herein, "mammalian stem cell" means a cell that may upon cell division retain the ability to self-renew and to give rise to at least one differentiated daughter cell. A mammalian stem cell includes a pluripotent stem cell, such as: an embryonic stem cell (ESC); an induced pluripotent stem cells (iPSC); and cells which have been transdifferentiated whereby the arising cell may upon cell division retain the ability to self-renew and to give rise to at least one differentiated daughter cell. In a particular embodiment a mammalian stem cell also includes adult tissue stem cells and any progenitor cells whether upstream or downstream thereof.

Lipid Supplement

In one aspect of this disclosure a lipid supplement for enhancing the survival or proliferation of one or more mammalian stem cells is provided. The lipid supplement may comprise one or more lipids.

In some embodiments of the lipid supplement, the one or more lipids may be selected from the group comprising: a fatty acid; a glycerolipid; a glycerophospholipid; a sphingolipid; a sterol lipid; a prenol lipid; a saccharolipid; or a polyketide.

In other embodiments of the lipid supplement, the one or more lipids may include a lipid-like substance, such as a poloxamer. The poloxamer may be Kolliphor™, Synperonics™, or Pluronics™. In certain embodiments, the lipid-like substance may be Kolliphor™ P188.

In other embodiments of the lipid supplement, the lipid supplement may include non-lipid components such as vitamins or derivatives or analogues thereof. Examples of vitamins that may be included in the lipid supplement include vitamin A, vitamin B, vitamin C, vitamin D, and vitamin E. Examples of vitamin derivatives or analogues may include d-alpha tocopherol, d-alpha tocopheryl acetate, d-alpha tocopheryl succinate, D-L-alpha-tocopherol, and LA2P.

In still other embodiments of the lipid supplement, the one or more lipids may be selected from the group comprising: a fatty acid; a glycerolipid; a glycerophospholipid; a sphingolipid; a sterol lipid; a prenol lipid; a saccharolipid; or a polyketide, and may also include a lipid-like substance, such as a poloxamer. The poloxamer may be Kolliphor™, Synperonics™, or Pluronics™. In certain embodiments, the lipid-like substance may be Kolliphor™ P188.

Still further, the lipid supplement may include non-lipid components such as vitamins or derivatives or analogues thereof. Examples of vitamins that may be included in the lipid supplement include vitamin A, vitamin B, vitamin C, vitamin D, and vitamin E. Examples of vitamin derivatives or analogues may include d-alpha tocopherol, d-alpha tocopheryl acetate, d-alpha tocopheryl succinate, D-L-alpha-tocopherol, and LA2P.

In a preferred embodiment of the lipid supplement, the one or more lipids include at least one fatty acid. In a specific embodiment, the one or more lipids include more than one fatty acid. The at least one fatty acid may be a saturated fatty acid or an unsaturated fatty acid. Or, the more than one fatty acid may include a plurality of saturated fatty acids, a plurality of unsaturated fatty acids, or a combination of at least one saturated fatty acid and at least one unsaturated fatty acid.

In embodiments of the lipid supplement where the one or more lipids include at least one fatty acid, the at least one fatty acid may be selected from the group of saturated fatty acids comprising propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, or octatriacontanoic acid, and/or from the group of unsaturated fatty acids comprising α-linolenic acid, stearidonic acid, eicosapentaenoic acid, docosahexaenoic acid, linoleic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, or mead acid.

In embodiments of the lipid supplement where the one or more lipids include more than one fatty acid, the plurality of saturated fatty acids may be selected from the group comprising propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, or octatriacontanoic acid; or the plurality of unsaturated fatty acids may be selected from the group comprising α-linolenic acid, stearidonic acid, eicosapentaenoic acid, docosahexaenoic acid, linoleic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, or mead acid; or the combination of at least one saturated fatty acid and at least one unsaturated fatty acid may be selected from the group comprising propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, octatriacontanoic acid, α-linolenic acid, stearidonic acid, eicosapentaenoic acid, docosahexaenoic acid, linoleic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, or mead acid.

In a specific embodiment of the lipid supplement, the one or more lipids are selected from the group comprising Mead's acid, arachidic acid, palmitoleic acid, oleic acid, myristic acid, palmitic acid, myristoleic acid, linoleic acid, stearic acid, α-linolenic acid, arachidonic acid, cholesterol, DL-α-tocopheryl, Kolliphor P188.

In a more specific embodiment of the lipid supplement, the one or more lipids include three or more of palmitic acid, stearic acid, oleic acid, linoleic acid, and α-linolenic acid.

In a still more specific embodiment of the lipid supplement, the one or more lipids of the lipid supplement include palmitic acid and oleic acid.

In embodiments where the lipid supplement may include more than one fatty acid, the more than one fatty acid may include a saturated fatty acid or an unsaturated fatty acid, or both. The more than one fatty acid may be selected from the group comprising propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, octatriacontanoic acid, α-linolenic acid, stearidonic acid, eicosapentaenoic acid, docosahexaenoic acid, linoleic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, or mead acid.

In a particular embodiment of the lipid supplement, the one or more lipids is not arachidonic acid or α-linolenic acid, or both.

In a different embodiment of the lipid supplement, the lipid supplement comprises only one lipid. The only one lipid may be selected from the group comprising: a fatty acid; a glycerolipid; a glycerophospholipid; a sphingolipid; a sterol lipid; a prenol lipid; a saccharolipid; or a polyketide.

In other embodiments of the lipid supplement, the only one lipid may include a lipid-like substance, such as a poloxamer. The poloxamer may be Kolliphor™, Synperonics™, or Pluronics™. In certain embodiments, the lipid-like substance may be Kolliphor™ P188.

In a specific embodiment of the lipid supplement, the only one lipid may be a fatty acid. In such embodiment, the fatty acid may be a saturated fatty acid. The saturated fatty acid may be selected from the group comprising propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, or octatriacontanoic acid.

In a different such embodiment, the fatty acid may be an unsaturated fatty acid. The unsaturated fatty acid may be selected from the group comprising α-linolenic acid, stearidonic acid, eicosapentaenoic acid, docosahexaenoic acid, linoleic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, or mead acid.

In a specific embodiment of the lipid supplement, the only one lipid may be selected from the group comprising Mead's acid, arachidic acid, palmitoleic acid, oleic acid, myristic acid, palmitic acid, myristoleic acid, linoleic acid, stearic acid, α-linolenic acid, arachidonic acid, cholesterol, DL-α-tocopheryl, Kolliphor P188.

In a more specific embodiment of the lipid supplement, the only one lipid may be selected from the group comprising palmitic acid, stearic acid, oleic acid, linoleic acid, and α-linolenic acid.

In a still more specific embodiment of the lipid supplement, the only one lipid is either palmitic acid or oleic acid.

In a particular embodiment of the lipid supplement, the only one lipid is not arachidonic acid or α-linolenic acid.

Certain lipid profiles may be better suited to the culture of certain cell types. In one embodiment, a lipid profile higher in oleic acid, palmitic acid, and linoleic acid than in stearic acid and α-linolenic acid may enhance the survival or proliferation of one or more mammalian stem cells. In the same or a different embodiment, a lipid profile for enhancing the survival or proliferation of one or more mammalian stem cells comprises one or more of oleic acid, palmitic acid, linoleic acid, stearic acid, and/or α-linolenic acid at a level higher than any other of the one or more lipids.

The skilled person will appreciate that using routine trial and error it would be possible to identify beneficial or detrimental one or more lipids, whether singly or in combination, for use in a lipid supplement to enhance the survival or proliferation of one or more cells.

It may be further desired to load each of the one or more lipids onto a carrier at the same or different concentrations. For example, the one or more lipids may be loaded onto the carrier to a concentration ranging from 1 ng/mL to 35 ug/mL. In the alternative, the one or more lipids may be loaded onto the carrier in accordance with the narrowed concentration range as indicated in Table 1.

In order to enhance the proliferation or survival of one or more mammalian stem cells, a carrier may be required to transport some or all of the lipid supplement to such cells, whether in vitro or in vivo. Thus, a lipid supplement for enhancing the survival or proliferation of one or more mammalian stem cells may comprise one or more lipids in the presence of a carrier.

Such a carrier could be any biological or non-biological agent, substance, composition or complex that is capable of transporting some or all of the lipid supplement to a cell. More specifically, the carrier is capable of transporting one or more lipids of the lipid supplement to a cell.

By way of non-limiting examples, a carrier may be an albumin, a micelle, a liposome, an extracellular vesicle, an exosome, a cyclodextrin, a nanostructured lipid carrier, or otherwise.

In embodiments where the carrier is an albumin, the albumin may be from any source. Many types of albumin are known in the field of cell culture. In addition, particular albumins may be better suited for culturing stem cells. The different types of albumins may vary depending on factors, such as their origin. For example, the albumin may be a bovine albumin (BSA), a human albumin (HSA), or otherwise. Or, the albumin may be a recombinant albumin. For example, the recombinant albumin may be a recombinant human albumin (rHA) or a recombinant bovine albumin (rBA).

In embodiments where the carrier is a liposome or an extracellular vesicle, such as an exosome, the one or more lipids may be present within the lipid bilayer thereof, or as cargo packaged within an internal space bounded by the lipid bilayer thereof.

Carriers of the disclosure may be purchased from a commercial entity or may be isolated/synthesized using commercially available products or reagents. For carriers that are naturally-occurring, such as extracellular vesicles (including exosomes), liposomes, micelles, and albumins, for example, such naturally-occurring carriers may be isolated using any established/available protocol. For carriers that are not necessarily naturally-occurring but are readily synthesizable, such as liposomes, micelles, cyclodextrins, nanostructured lipid carriers, or otherwise, such not naturally-occurring carriers may be synthesized using any established/available protocol.

Some or all carriers may be purchased from a commercial entity. Specifically, powdered or solubilized albumin may be purchased from any vendor, such as ThermoFisher Scientific, Sigma-Aldrich, or otherwise.

Whether isolated, manufactured or purchased, the carriers of the disclosure may from the outset comprise one or more lipids or fatty acids. Such one or more lipids or fatty acids may be present at appreciable levels or at levels either very close to a detection limit or below the detection limit, and therefore at essentially undetectable levels.

Where a specific lipid profile is required to affect a desired outcome, the presence of one or more lipids or fatty acids in association with the carrier at the outset may be problematic if, for example, the lipid profile is not amenable to affecting the desired outcome. Accordingly, in certain embodiments it may be desirable to remove or deplete some or all of such one or more lipids or fatty acids from the carrier.

In another embodiment, the one or more lipids may be loaded onto a lipid-free or a lipid-reduced carrier, such as an albumin. Regardless of whether or not the carrier is lipid-free, lipid-reduced, or otherwise, the carrier may be loaded with a desired one or more types of lipids, generating a lipid-enriched carrier having a defined lipid signature.

In other embodiments, whether isolated, synthesized, or purchased, the carrier may be free of lipids or fatty acids or substantially free of lipids or fatty acids.

In one embodiment of enhancing the survival or proliferation of one or more mammalian stem cells, the one or more lipids (or the at least one fatty acid) and/or lipid-like substances may be pre-loaded onto a carrier. The one or more lipids (or the at least one fatty acid) and/or lipid-substances may be pre-loaded onto the carrier using any conventional technique known in the field. For example, pre-loading the one or more lipids and/or lipid-substances onto the carrier may be carried out by combining a desired amount of each desired one or more lipids (or at least one fatty acid) and/or lipid-substances with a desired amount of the carrier and incubating such combination for a time sufficient to allow the one or more lipids (or at least one fatty acid) and/or lipid-substances and the carrier to come to an equilibrium, or substantially to an equilibrium. Exposing one or more mammalian stem cells to a thusly prepared carrier pre-loaded with one or more lipids (or at least one fatty acid) and/or lipid-substances may enhance the survival or proliferation of the one or more mammalian stem cells.

In another embodiment, the one or more lipids (or the at least one fatty acid) and/or lipid-substances may be combined but not necessarily pre-loaded onto the carrier. For example, combining the one or more lipids (or the at least one fatty acid) and/or lipid-substances with the carrier may be carried out by combining a desired amount of each desired one or more lipids (or at least one fatty acid) and/or lipid-substances with a desired amount of the carrier without allowing the carrier and the one or more lipids (or at least one fatty acid) and/or lipid-substances to come to an equilibrium. Such a combination of the one or more lipids (or at least one fatty acid) and the carrier may be incubated without allowing the combination to come to an equilibrium. Exposing one or more mammalian stem cells to a thusly combined carrier and one or more lipids (or at least one fatty acid) and/or lipid-substances may enhance the survival or proliferation of the one or more mammalian stem cells.

In another embodiment, the one or more lipids (or the at least one fatty acid) and/or lipid-substances may be provided separate from the carrier to a cell culture of one or more mammalian stem cells. Providing the one or more lipids (or the at least one fatty acid) and/or lipid-substances separate from carrier to a cell culture of one or more mammalian stem cells can be accomplished in any order. For example, the carrier may already be present in the cell culture and the one or more lipids (or the at least one fatty acid) and/or lipid-substances are added afterward. Or, the one or more lipids (or the at least one fatty acid) and/or lipid-substances may already be present in the cell culture and the carrier is added afterward. Or, neither the carrier nor the one or more lipids and/or lipid-substances are already present in the culture, and both components may be added in any sequence with any or no time delay between addition steps to the cell culture.

In certain embodiments, free one or more lipids (or at least one fatty acid) and/or lipid-substances may be spiked into a cell culture already comprising a carrier. Spiking the free one or more lipids and/or lipid-substances could be achieved using any quantity and/or combination of the free one or more lipids, provided that the spiked free one or more lipids and/or lipid-substances is not detrimental to the survival or proliferation of the one or more mammalian stem cells in the cell culture. Preferably, the spiked free one or more lipids and/or lipid-substances enhance the survival or proliferation of the one or more mammalian stem cells in the cell culture.

In a further embodiment, it may be advantageous to spike additional carrier into the cell culture along with the free one or more lipids (or at least one fatty acid) and/or lipid-substances.

Culture Media

In one aspect of this disclosure culture media for enhancing the survival or proliferation of one or more cells cultured therein is provided. In certain embodiments the one or more cells may be one or more mammalian cells, and more specifically the one or more cells may be one or more mammalian stem cells. Various embodiments of a culture medium for enhancing the survival or proliferation of one or more cells are further described below.

In one embodiment, the culture medium comprises a lipid supplement as described herein. For example, the lipid supplement may comprise one or more lipids and/or lipid-substances, one or more lipids including at least one fatty acid, one or more lipids including more than one fatty acid, or only one lipid.

In the same embodiments or in a different embodiment of the culture medium, the lipid supplement may comprise one or more lipids and/or lipid-substances, one or more lipids including at least one fatty acid, one or more lipids including more than one fatty acid, or only one lipid, in the presence of a carrier.

In a specific embodiment of the culture medium, the one or more lipids and/or lipid-substances, the one or more lipids including at least one fatty acid, the one or more lipids including more than one fatty acid, or the only one lipid, in the presence of a carrier is a lipid-enriched carrier. The lipid-enriched carrier may be a lipid-enriched albumin.

In one embodiment of the lipid supplement of the culture medium, the one or more lipids and/or lipid-substances, the one or more lipids including at least one fatty acid, the one or more lipids including more than one fatty acid, or the only one lipid may be pre-loaded onto the carrier and added to culture medium whether prior to or after exposing the cells to the culture medium. The lipid-enriched carrier, such as a lipid-enriched albumin, may be prepared using known methods wherein powdered or solubilized carrier may be loaded with one or more lipids in accordance with the description below.

In another embodiment of the lipid supplement of the culture medium, the one or more lipids, the one or more lipids including at least one fatty acid, the one or more lipids including more than one fatty acid, or the only one lipid may be combined with a carrier in the culture medium, or in a separate solution, prior to exposing the cells to the culture medium. Or, the one or more lipids, the one or more lipids including at least one fatty acid, the one or more lipids including more than one fatty acid, or the only one lipid, and a carrier may each be added to the culture medium separately after the culture medium has been added to the cells.

In one embodiment, the culture medium comprises a lipid supplement as described herein and one or more survival factors. The one or more survival factors may be any molecule, compound, or otherwise that enhance the survival of the cultured mammalian stem cell. In turn, a mammalian stem cell having enhanced survival, may also demonstrate enhanced proliferation in the disclosed culture medium.

In one embodiment, the one or more survival factors may comprise one or more small molecule inhibitors. In certain embodiments, the one or more small molecule inhibitors may comprise one or more of Thiazovivin, Y-27632, CHIR99021, SB202190, MI-7, Necrostatin-1, NS3694, Wnt-059, NSCI, or BIPV5. In other embodiments, the one or more small molecule inhibitors may comprise a Rho/Rock pathway inhibitor. One example of a common Rho/Rock inhibitor is Y-27632.

The one or more survival factors of a disclosed culture medium, may be present in a concentration ranging from 1 nM to 1 mM. In a particular embodiment, the one or more survival factors such as Y-27632 is present at a concentration of 10 μM.

In another embodiment, the culture medium for enhancing the survival or proliferation of one or more mammalian stem cells may further comprise an extracellular matrix. The extracellular matrix may be a naturally derived matrix product, such as by way of non-limiting example, a product secreted by a cell or tissue. Or, the extracellular matrix may be a decellularized matrix.

In some embodiments, the extracellular matrix may comprise one or more monomatrix components. Non-limiting examples of monomatrix components include fibronectin, collagen, laminin, elastin, vitronectin, entactin, heparin sulphate, or proteoglycans alone or in combination. In other embodiments the extracellular matrix may be Matrigel™.

In embodiments where the culture medium comprises an extracellular matrix, a concentration of the extracellular matrix may be below a gelation threshold thereof. The gelation threshold may vary depending on the type of extracellular matrix (or matrix of one or more monomatrix components) added to the culture medium. Notwithstanding, the gelation threshold of an extracellular matrix (whether consisting of a monomatrix component or comprising one or more monomatrix components) is the point at which the culture medium forms a solid or substantially solid solution, rather than a liquid or a semi-solid solution. In embodiments where the extracellular matrix is Matrigel™, the gelation threshold is about 0.5% v/v or higher.

In another aspect, the present disclosure provides a culture medium for enhancing the survival or proliferation of one or more mammalian stem cells comprising an extracellular matrix component or components, and optionally comprising a lipid supplement as described herein.

According to one embodiment of such culture medium, the extracellular matrix may be a naturally derived matrix product, such as by way of non-limiting example, a product secreted by a cell or tissue. Or, the extracellular matrix may be a decellularized matrix.

In some embodiments, the extracellular matrix may comprise one or more monomatrix components. Non-limiting examples of monomatrix components include fibronectin, collagen, laminin, elastin, vitronectin, entactin, heparin sulphate, or proteoglycans alone or in combination. In other embodiments the extracellular matrix may be Matrigel™.

In embodiments where the culture medium comprises an extracellular matrix, a concentration of the extracellular matrix may be below a gelation threshold thereof. The gelation threshold may vary depending on the type of extracellular matrix (or matrix of one or more monomatrix components) added to the culture medium. Notwithstanding, the gelation threshold of an extracellular matrix (whether consisting of a monomatrix component or comprising one or more monomatrix components) is the point at which the culture medium forms a solid or substantially solid solution, rather than a liquid or a semi-solid solution. In embodiments where the extracellular matrix is Matrigel™, the gelation threshold is about 0.5% v/v or higher.

In one embodiment, the culture medium may further comprise one or more survival factors. The one or more survival factors may be any molecule, compound, or otherwise that enhance the survival of the cultured mammalian stem cell(s). In turn, a mammalian stem cell having enhanced survival, may also demonstrate enhanced proliferation in the disclosed culture medium.

Further details of the one or more survival factors may be gleaned from the description thereof hereinabove.

The culture media will also contain other factors necessary for the growth and survival of the stem cells. Media formulations or base media formulations appropriate for culturing particular types of mammalian stem cells are commercially available. Any such media formulation or base media formulation may be used to formulate the medium disclosed herein, and to carry out the methods disclosed herein.

In one embodiment, the culture medium may comprise growth factors that support the culture of mammalian cells.

In a particular embodiment applicable to hPSC, the growth factors may include, but are not limited to, SCF, EGF, TGFβ, FGF, LIF, and BMP.

The culture medium may also comprise other additives that support the culture of mammalian stem cells. In another embodiment, applicable to human stem cells, the other additives may include, but are not limited to, 4-aminobutyric acid, BSA, pipecolic acid, and lithium chloride.

Methods

Stem cells are commonly cultured in vitro. In such in vitro applications, it is preferable to culture stem cells under particular culture conditions. If in vitro stem cells are not cultured under particular culture conditions, the stem cells may grow sub-optimally. In some cases sub-optimal growth may comprise a decreased growth rate. In other cases, sub-optimal growth may comprise unintended differentiation of the stem cells. In still other cases, sub-optimal growth may comprise cell death, such as by apoptosis, necrosis, autophagy, or otherwise. The inventors have shown that culturing stem cells in a culture medium comprising a lipid supplement may enhance the survival or proliferation of one or more mammalian stem cells.

In one aspect, the present disclosure provides methods of enhancing the survival or proliferation of mammalian stem cells comprising culturing the stem cells in a culture medium comprising a lipid supplement as described herein.

In one embodiment, the present disclosure provides methods of enhancing the survival or proliferation of mammalian stem cells comprising culturing the stem cells in a culture medium comprising a lipid enriched carrier as described herein.

In a more specific embodiment, the present disclosure provides methods of enhancing the survival or proliferation of mammalian stem cells comprising culturing the stem cells in a culture medium comprising a lipid-enriched albumin.

In another embodiment, the culture media may also comprise other factors such as one or more survival factors as described herein.

In another embodiment, the present disclosure provides a method of enhancing the survival or proliferation of one or more mammalian stem cells comprising culturing the stem cells in a culture medium further comprising an extracellular matrix component or components.

In another aspect, the present disclosure provides a method of enhancing the survival or proliferation of mammalian stem cells comprising culturing the stem cells in a culture medium comprising an extracellular matrix component or components and optionally a lipid supplement as described herein.

In specific embodiments, the extracellular matrix component or components are provided below a gelation threshold thereof.

In one embodiment, the culture media may also comprise other factors such as one or more survival factors as described herein.

Accordingly, the present disclosure provides for methods of enhancing the survival or proliferation of one or more mammalian stem cells in a culture medium according to a medium as described hereinabove. Enhanced survival or proliferation may be calculated by any technique known in the art, including but not limited to determining a % cloning efficiency by dividing the number of colonies/clones generated by the number of input cells or clumps/clusters thereof. In certain embodiments, enhanced survival or proliferation comprises yielding a 5%-65% cloning efficiency. Or, enhanced survival or proliferation may be referenced by indicating the number of recovered clones/colonies from the inputted cells or clumps/clusters thereof.

The stem cells can be any mammalian stem cell that one wishes to culture to enhance the survival and proliferation of the cells.

In this disclosure, stem cells can be any mammalian stem cell. In one embodiment, the stem cells are non-rodent. For example, the non-rodent mammalian stem cells may be porcine stem cells. In the alternative, the non-rodent mammalian stem cells may be primate stem cells. In the further alternative, the primate stem cells may be human stem cells.

The skilled person will also be aware that the mammalian stem cells may correspond to any developmental stage of the mammal. For example, the mammalian stem cells may be embryonic in origin, such as embryonic stem cells (ESC). In the alternative, the mammalian stem cells may originate from a tissue or organ of an adult mammal. Or, the mammalian stem cell may be an induced pluripotent stem cell (iPSC), wherein the iPSC may be generated using any technique known in the art. Collectively, ESC and iPSC are termed pluripotent stem cells (PSC).

In view of the potential downstream applications of in vitro cultured mammalian stem cells, particularly those cultured by seeding one or more mammalian stem cells as single cells, it may be desirable that the mammalian stem cells have a normal karyotype. It may be further desirable that the normal karyotype is stable. A normal karyotype may be characterized by an appropriate number of chromosomes characteristic for a species. In addition or in the alternative, a normal karyotype may be characterized by a proper staining profile, using any stain known in the art for banding analysis of chromosomes, such as Giemsa. In further addition or in the further alternative, a normal karyotype may be characterized by properly sized chromosomes.

In another embodiment, the mammalian stem cells are genetically engineered. Mammalian stem cells may be genetically engineered using any technology known in the art. For example, a mammalian stem cell may be genetically engineered using gene editing technology. Gene editing technology may include, but is not limited to, CRISPR technology, zinc-finger nuclease technology, TALEN technology or ARCUS technology.

The problems associated with the expansion and/or survival of mammalian stem cells are heightened when it is desirable to genetically-engineer the mammalian stem cells. For example, when one or more mammalian stem cells are subjected to gene editing technology, it is likely that no two mammalian stem cells are identically genetically-engineered. However, if such genetically-engineered mammalian stem cells will be used in downstream applications, regardless of whether the applications are in vivo or in vitro, it is preferable to use a clonal population thereof obtained, for example, by seeding one or more mammalian stem cells as single cells.

The disclosed methods may comprise providing a population or culture of mammalian stem cells. Or, the disclosed methods may comprise providing one or more mammalian stem cells. The provided mammalian stem cells may have been maintained in any culture media known in the art. The type of culture media for maintaining the mammalian stem cells will depend on the nature of the mammalian stem cells. As indicated above, the mammalian stem cells may be embryonic in origin. Alternatively, the mammalian stem cells may originate from an adult tissue or organ. In the further alternative, the mammalian stem cell may have been induced or transdifferentiated from a suitable parental cell. The type of medium used to maintain the mammalian stem cell will also depend on the species from which the mammalian stem cell originates. For example, human PSC (hPSC), may be maintained in an mTeSR™ media formulation.

In one embodiment, the stem cells are cultured for 6-8 days after passaging and then are dissociated to single cells and seeded into the culture medium comprising the lipid supplement and optionally the one or more survival factors. In a specific embodiment, the cells are seeded at a density of 1 cell/well up to 1000 cells/well. The cells are then fed again at day 2 with the medium comprising the lipid supplement and optionally the one or more survival factors then fed at day 4 with the regular growth medium (total of 4 days in cloning supplement (ie. lipid supplement)). The cells can then be fed daily until the colonies are harvested, such as around 7-12 days.

In another embodiment, the stem cells may be cultured for 6-8 days after passaging and then dissociated to single cells and seeded into the culture medium comprising one or both of a lipid supplement or an extracellular matrix component or components, and optionally the one or more survival factors. In a specific embodiment, the cells may be seeded at a density of 1 cell/well up to 1000 cells/well. The cells may then be fed again at day 2 with the medium comprising one or both of the lipid supplement or the extracellular matrix component or components, and optionally the one or more survival factors then fed at day 4 with the regular growth medium (total of 4 days in cloning supplement (ie. lipid supplement)). The cells can then be fed daily until the colonies are harvested, such as around 6-12 days.

The skilled person will be aware that the number of days for exposing the one or more mammalian stem cells to the lipid supplement and/or the extracellular matrix component or components is merely a guideline and could readily be varied. Such exposure may be longer or shorter in duration than the 2 days suggested above. For example, such exposure could be less than 2 days, such as approximately 36 hours, 24 hours, 18 hours, 12 hours, 8 hours, 6 hours, 4 hours, 2 hours, 1 hour, or less. Or, such exposure could be for longer than 2 days. For example, the longer than 2 day exposure may be up to the total amount of time the one or more mammalian stem cells may be cultured in the same medium, without undergoing a change of medium.

Further, exposure of the one or more mammalian stem cells to the lipid supplement and/or the extracellular matrix component or components may occur any number of times. For example, the one or more mammalian stem cells may only require a single exposure to the lipid supplement and/or extracellular matrix component or components. Such single exposure could be for any appropriate amount of time, as specified above. Or, the one or more mammalian stem cells may require two or more exposures to the lipid supplement and/or extracellular matrix component or components.

In another specific embodiment, the cells may be fed daily via fedbatch feeding at day 2 with the regular growth medium or a medium comprising one or both of the lipid supplement or the extracellular matrix component or components, and optionally the one or more survival factors. The cells can then be fed daily until the colonies are harvested, such as around 4-10 days.

The provided mammalian stem cells may be sub-cultured once the mammalian stem cells achieve threshold confluency. Or, the provided mammalian stem cells may be sub-cultured as dictated by colony health, such as may be determined by colony appearance, size or morphology.

Sub-culturing the provided mammalian stem cells may be performed using any technique, appropriate to the particular culture of mammalian stem cells, known in the art of stem cell culture. For example, once hPSC achieve a confluency of approximately 70% it may be desirable to sub-culture the cells into a different culture vessel.

Typically, an hPSC culture at an appropriate level of confluency and/or having a particular colony size may be detached from a culture vessel by applying a suitable agent. The agent may comprise digestive enzyme(s) or chemicals known in the field to detach colonies. If a digestive enzyme(s) is used, it may be desirable to inactivate the digestive enzyme(s) by the addition of a second inactivating solution. In order to further disaggregate the detached mammalian stem cells, it may be necessary to expose them to an agitative force, such as by repetitive upward and downward pipetting or by a technician mechanically striking the culture vessel.

Upon sufficient agitation, the detached, disaggregated mammalian stem cells may exist as a single cell suspension or as clusters having desirable dimensions, which may comprise a desired cell number range. Sufficiently disaggregated cells may be sub-cultured at a desired cell density, by plating one or more of the mammalian stem cells in an appropriate culture vessel.

Plating the desired cell density of the one or more mammalian stem cells may be performed using any known method. A single cell suspension of the mammalian cells or a suspension of cell clusters may be plated using conventional techniques. For example, after determining the cell density of the suspension, an appropriate volume of the suspension may be used to seed a culture vessel, or a well or microwell thereof. Or, the cell suspension can be subjected to fluorescence activated cell sorting, and the sorted mammalian cells may be appropriately partitioned, at an appropriate cell number, into a culture vessel, or a well or microwell thereof.

In certain applications, it may be desirable to seed the mammalian stem cells by plating only a single mammalian cell into a culture vessel, or a well or microwell thereof. Or, it may be desirable to seed the mammalian stem cells by plating single mammalian cells at a sufficiently low density into a culture vessel, or a well or microwell thereof. In such circumstances, it is desirable that the cell density is sufficiently low to minimize the tendencies of the plated mammalian cells to aggregate, such as by ensuring sufficient spacing between cells in the culture vessel, or a well or microwell thereof. Also, such sufficient spacing may minimize paracrine signaling among the mammalian stem cells in the culture vessel, or well or microwell thereof.

In one embodiment, a single hPSC may be plated in a single well or microwell of a culture vessel. The single hPSC may be plated after having determined the cell density of the detached, disaggregated population of hPSC and plating an appropriate volume. Or, the single hPSC may be plated using cell sorting technology, such as fluorescence activated cell sorting. In another embodiment, one or more hPSC may be plated at a clonal density in a relatively larger culture vessel, or well thereof. For example, a clonal density may comprise a density of between 1 cell/well to 1000 cells/cm$^2$.

Overall, the presently disclosed methods may encompass culturing the one or more mammalian stem cells in a culture medium of this disclosure as a monolayer (ie. adherent culture) or as a non-adherent-culture (ie. in suspension). Regardless of whether the one or more mammalian stem cells are seeded as a monolayer or as a non-adherent culture, the disclosed methods may further comprise seeding the one or more cells at a seeding density of 1 cell/well up to about 1000 cells/cm$^2$). In some embodiments the one or more mammalian stem cells may be seeded as a single cell.

In embodiments wherein the one or more mammalian stem cells are cultured as a monolayer, culturing as a monolayer may comprise seeding the one or more cells in an extracellular matrix.

In another embodiment, mammalian stem cells may be plated, whether as single cells or as clusters, with a view to culturing the one or more plated mammalian cells either as a suspension or an adherent culture.

Where it may be desired to culture the mammalian stem cells as a suspension culture, whether as single cells or as clusters, it may be desirable to seed mammalian cells as clumps of cells or a single cell suspension directly into a bioreactor, spinner flask, suspension culture plate or other such vessel that promotes the growth of stem cells in suspension. It may also be desirable to pre-aggregate the stem cells using micro-well plates or any other such method to create equally sized aggregates before plating stem cells into the aforementioned vessels. It may also be desirable to culture the cells in the presence of micro carriers to support the growth of stem cells in suspension.

Where it may be desired to culture the mammalian stem cells as an adherent culture, whether as single cells or as clusters, it may be desirable to plate the one or more mammalian stem cells onto a suitable matrix. The matrix may be any matrix that supports the culture of the one or more mammalian stem cells. The matrix may also promote attachment of the one or more mammalian stem cells. For example, the matrix may comprise extracellular matrix proteins that support the culture of the one or more mammalian stem cells. Various matrices comprising extracellular matrix proteins are commercially available, such as Matrigel. Examples of some extracellular matrix proteins contemplated in this disclosure include laminin, collagen, fibronectin, vitronectin, or entactin. The matrix contemplated in this disclosure may further comprise known quantities of a combination of extracellular matrix proteins, such as laminin, collagen, fibronectin, vitronectin, entactin, or otherwise.

The plated one or more mammalian stem cells, whether cultured in suspension or as an adherent culture, should be supplemented with a culture medium that supports the culture thereof, such as a culture medium of this disclosure. As indicated above, culture conditions may vary depending on the nature and characteristics of the mammalian stem cells. The skilled person will understand that the culture medium for supporting the culture of the mammalian stem cells should comprise a base medium formulation appropriate to the nature and characteristics of the mammalian stem cells.

In one embodiment, hPSC may be maintained and sub-cultured in a mTeSR™ formulation, such as mTeSR™ 1, mTeSR™2, TeSR™-E8 or mTeSR™3D. mTeSR™ formulations are well-suited to standard culturing of hPSC. In other embodiments, hPSC may be maintained and sub-cultured in knock-out serum replacement (KOSR) based medium, StemMACS™ iPS-Brew (Miltenyi Biotec) iPS-Brew, Essential 8™ Medium (Thermo Fisher Scientific), Essential-8, StemFlex™ Medium (Thermo Fisher Scientific), Cellartis® DEF-CS™ (Takara) or other medium to support the growth of stem cells.

In another embodiment, adult human stem cells, such as mesenchymal stem cells may be maintained and sub-cultured in MesenCult™-XF, MesenCult™-ACF, or MesenCult™-PL, for example.

In another embodiment, adult human stem cells, such as neural stem cells may be maintained and sub-cultured in NeuroCult™, BrainPhys™, or Xcell Neural Medium, for example.

By culturing the one or more non-rodent mammalian cells with a medium comprising a lipid-enriched albumin and optionally one or more survival factors, it may be possible to yield a 5% to 65% survival rate for the one or more cells cultured with the medium.

TABLE 1

Concentration of fatty acids on lipid-enriched albumin.

| Fatty Acid | Narrowed Range | Broad Range |
| --- | --- | --- |
| Mead's acid | 0.006-0.371 µg/mL | 1 ng/mL-35 µg/mL |
| Arachidic | 0.054-1.457 µg/mL | 1 ng/mL-35 µg/mL |
| Palmitoleic | 0.054-1.817 µg/mL | 1 ng/mL-35 µg/mL |
| Oleic | 0.965-33.576 µg/mL | 1 ng/mL-35 µg/mL |
| Myristic | 0.033-1.16.5 µg/mL | 1 ng/mL-35 µg/mL |
| Palmitic | 1.115-35.129 µg/mL | 1 ng/mL-35 µg/mL |
| Myristoleic | 0.103-0.536 µg/mL | 1 ng/mL-35 µg/mL |
| Linoleic | 1.734-23.907 µg/mL | 1 ng/mL-35 µg/mL |
| Stearic | 0.273-3.979 µg/mL | 1 ng/mL-35 µg/mL |
| alpha-linolenic | 0.022-1.709 µg/mL | 1 ng/mL-35 µg/mL |

The following non-limiting examples are illustrative of the present disclosure:

EXAMPLES

Example 1

12-well culture plates were coated with 0.5 mL of cloning matrix or extracellular matrix (1:25 dilution in CellAdhere™ Dilution Buffer) and placed at room temperature for 1 hour. The matrix was then aspirated and 1 mL of media (mTeSR™1 or TeSR™-E8™ supplemented with either 10 µM Y27632 or media comprising lipid-enriched albumin, GABA, pipecolic acid, lithium chloride, FGF, TGFβ and Y-27632 (hereafter termed cloning supplement)) was added to each well and the plate was placed at 37° C. for 1 hour. hPSC lines were dissociated to single cells and seeded into the pre-warmed plates at 25 cells/cm$^2$ and placed at 37° C. for two days. The cells were then fed with fresh media (mTeSR™1 or TeSR™-E8™ supplemented with either 10 µM Y-27632 or cloning supplement) and placed at 37° C. for two days. On day four the cells were then fed with 1 mL of mTeSR™1 or TeSR™-E8™ without additives and fed daily until day seven. Cells were then fixed using 4% paraformaldehyde and stained for alkaline phosphatase. Undifferentiated colonies were then counted and cloning efficiency was determined using the following calculation: (Number of undifferentiated colonies at day seven (per well)/Number of cells seeded at day zero (per well))×100. (Error bars represent standard deviation from three biological replicates).

The results of this Example are shown in FIG. 1 and demonstrate that each hPSC line (H1, H7, WLS-1C, STiPS-M001) plated at clonal density (25 cells/cm$^2$) shows enhanced cloning efficiency when grown in mTeSR™1 or TeSR™-E8™ when mTeSR™1 and TeSR™-E8™ are supplemented with cloning supplement, but not when grown in mTeSR™1 or TeSR™-E8™ supplemented with Rock inhibitor alone.

Example 2

96-well culture plates were coated with 50 µL of cloning matrix or extracellular matrix (1:25 dilution in CellAdhere™ Dilution Buffer) and placed at room temperature for 1 hour. The matrix was then aspirated and 100 µL of media (mTeSR™1 supplemented with either 10 µM Y-27632 or cloning supplement was added to each well and the plate was placed at 37° C. for 1 hour. hPSC lines were dissociated to single cells and sorted using a BD FACSAria™ Fusion at 1 cell/well and placed at 37° C. for two days. The cells were then fed with fresh media (mTeSR™1 supplemented with either 10 µM Y-27632 or cloning supplement) and placed at 37° C. for two days. On day four the cells were then fed with 100 µL mTeSR™1 without additives and fed daily until day seven. Cells were then fixed using 4% paraformaldehyde and stained for alkaline phosphatase. Undifferentiated colonies were then counted and cloning efficiency was determined using the following calculation: (Number of undifferentiated colonies (per plate)/Number of wells seeded (at 1 cell per well))×100. (Error bars represent SEM from two technical replicates).

Figure 2:
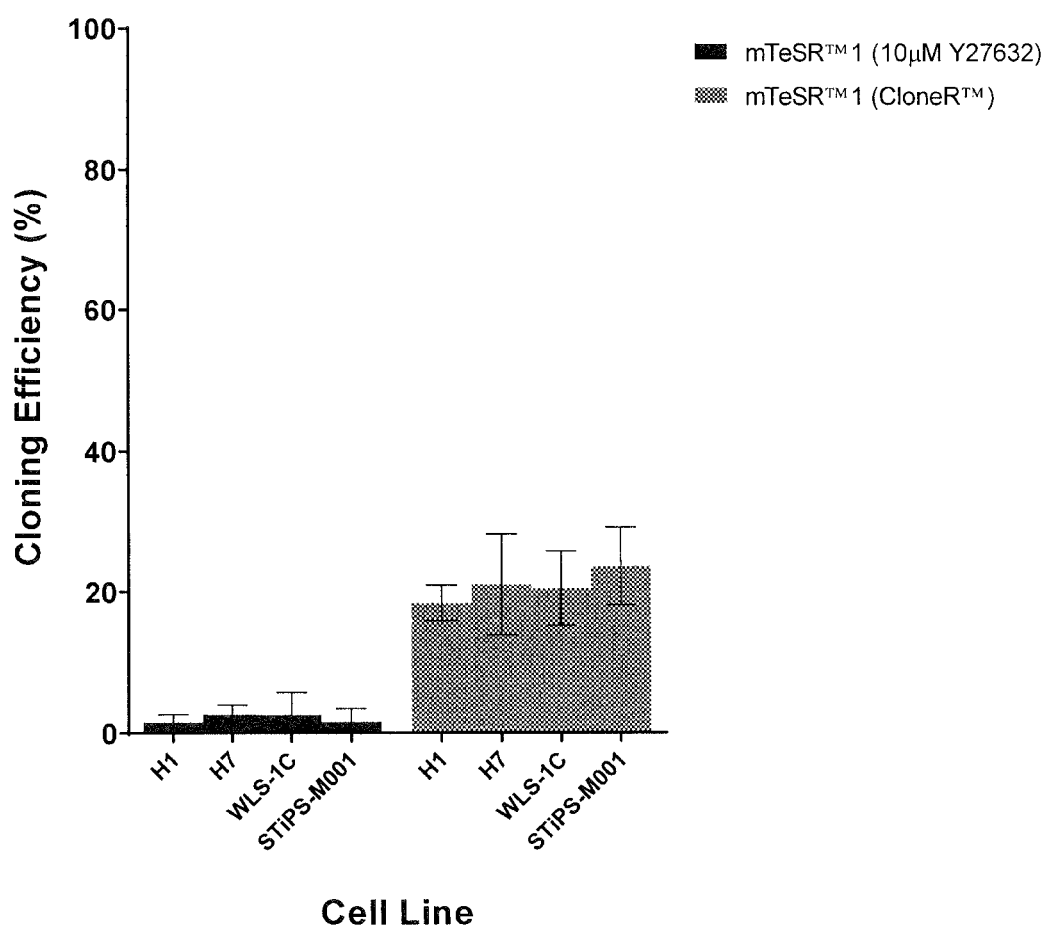
FIG. 2 is a bar graph showing the % cloning efficiency for various cell lines cultured in different culture media.

The results of this Example are shown in FIG. 2 and demonstrate that each hPSC line (H1, H7, WLS-1C, STiPS-M001) plated at a density of one cell per well shows enhanced cloning efficiency when grown in mTeSR™1 or TeSR™-E8™ when mTeSR™1 and TeSR™-E8™ are supplemented with cloning supplement, but not when grown in mTeSR™1 or TeSR™-E8™ supplemented with Rock inhibitor alone.

Example 3

Eight independent WLS-1C clones were manually picked 10 days following single cell deposition (from Example 2) and expanded for 5 passages using mTeSR™1 and passaged using Gentle Cell Dissociation Reagent (full protocol available stemcell.com). Total number of clumps per well were counted at the end of each passage to determine the daily fold expansion of the cloned lines compared to the clump passaged control. Daily fold expansion was determined using the following calculation: (total number of clumps at the end of passage/number of colonies seeded at the beginning of passage)/number of days in culture. (Error bars represent data from at least two biological replicates).

Figure 3:
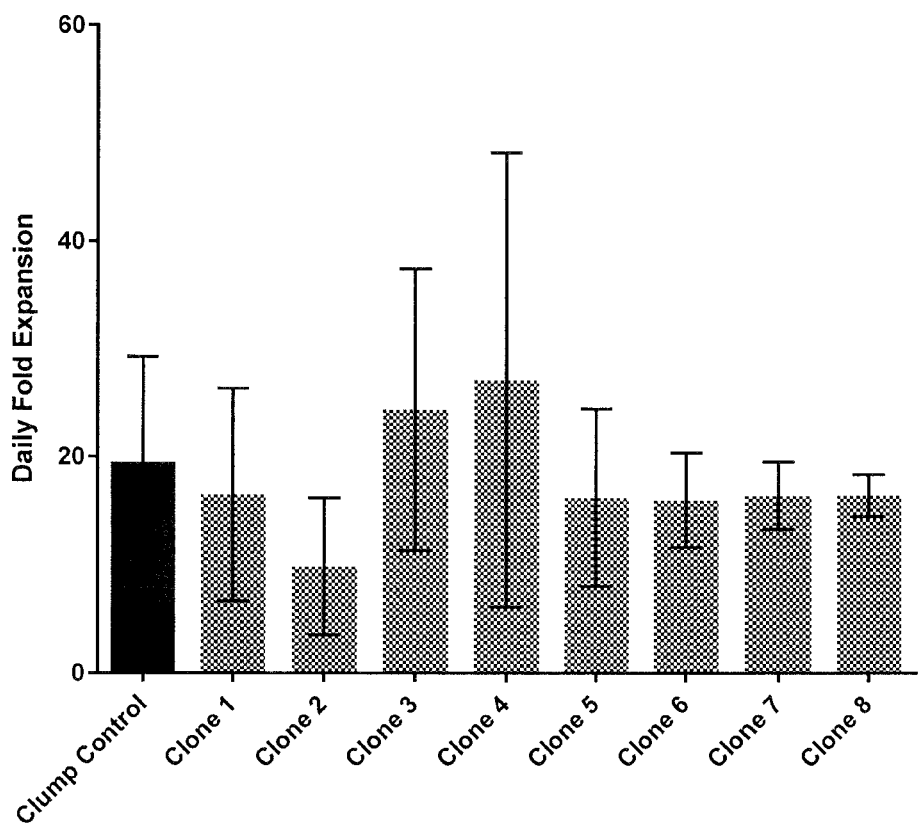
FIG. 3 is a graph showing the daily fold expansion for various WLS-1C human stem cell clones as compared to the clump passaged control.

The results of this example are shown in FIG. 3 and demonstrate that eight independent WLS-1C clones formed under conditions described in Example 2 exhibit a daily fold expansion comparable to hPSC cultured conventionally as clumps.

Example 4

12-well culture plates were coated with 0.5 mL of cloning matrix or extracellular matrix (1:25 dilution in CellAdhere™ Dilution Buffer) and placed at room temperature for 1 hour. The matrix was then aspirated and 1 mL of test media was added to each well. The different test media consisted of control media (mTeSR™1 supplemented with 10 µM Y-27632), or mTeSR™1 supplemented with media comprising cloning supplement made with lipid enhanced BSA, or mTeSR™1 supplemented with cloning supplement with lipid stripped BSA that had either been lipid loaded with ethanol only, three fatty acids or five fatty acids. The plate was then placed at 37° C. for 1 hour. hPSC lines were dissociated to single cells and seeded into the pre-warmed plates at 25 cells/cm² and placed at 37° C. for two days. The cells were then fed with the corresponding test media and placed at 37° C. for two days. On day four the cells were then fed with 1 mL of mTeSR™1 without additives and fed daily until day eight. Cells were then fixed using 4% paraformaldehyde and stained for alkaline phosphatase. Undifferentiated colonies were then counted and cloning efficiency was determined using the following calculation: (Number of undifferentiated colonies at day seven (per well)/Number of cells seeded at day zero (per well))×100. (Error bars represent SEM from three technical replicates).

Figure 4:
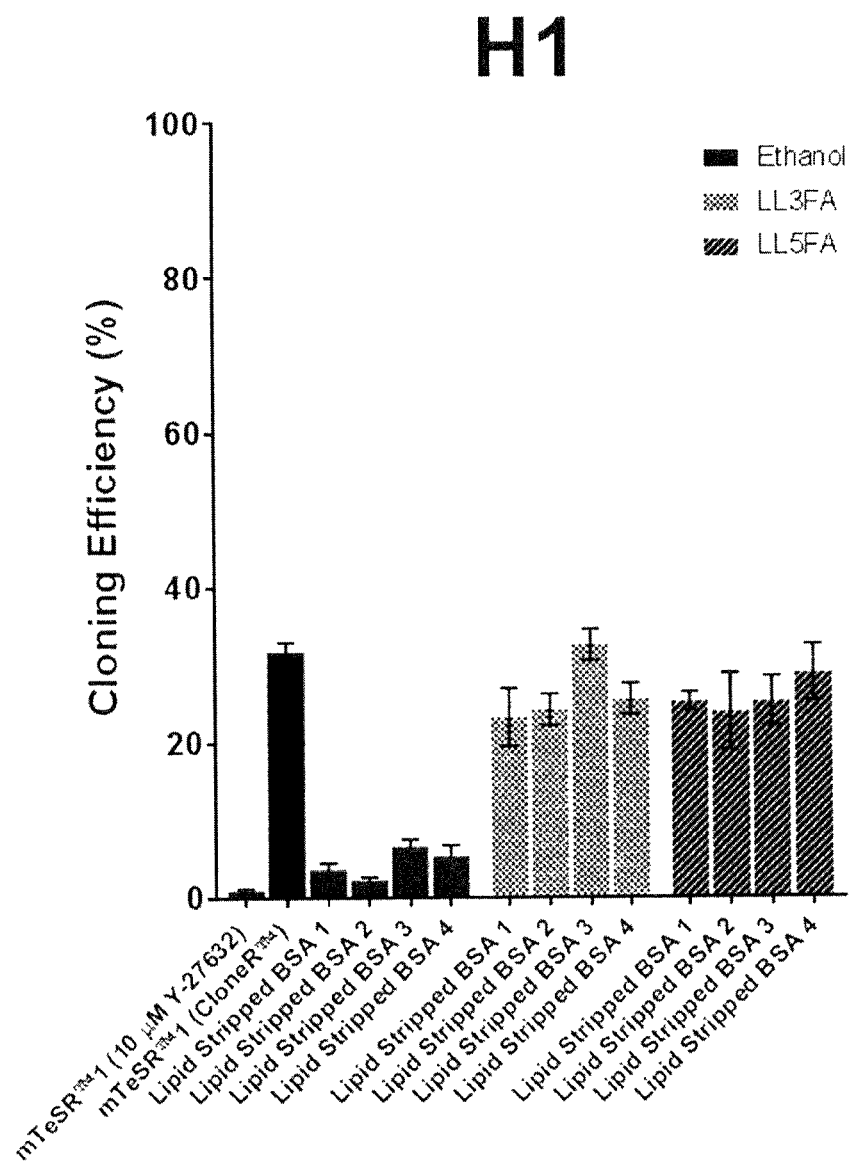
FIG. 4 is a bar graph showing the % cloning efficiency of hPSC in various culture media.
Figure 5:
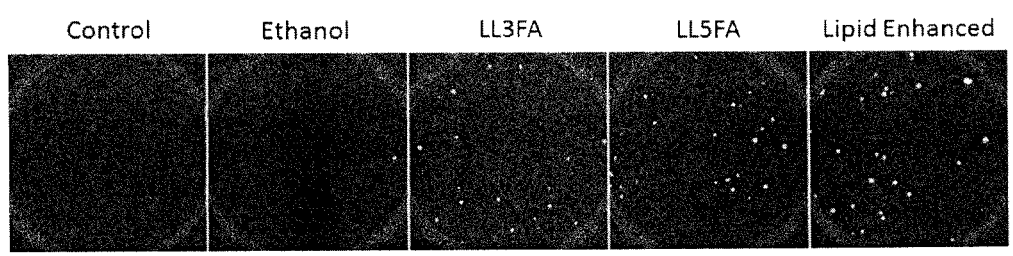
FIG. 5 shows representative images of wells from Example 4 stained with alkaline phosphatase.

The results of this example are shown in FIG. 4 and demonstrate that H1 hPSC grown in mTeSR™1 supplemented with Rock inhibitor and a lipid-stripped BSA loaded with either oleic, palmitic, and linoleic (3FA) or oleic, palmitic, linoleic, stearic and alpha-linoleic (5FA) at 600 µg/g (per fatty acid), exhibit enhanced cloning efficiency comparable to a purchased lipid enhanced BSA, but not for lipid stripped BSA loaded with ethanol (control).

Example 5

Representative images of wells from Example 4 (Lipid-stripped BSA 1) stained with alkaline phosphatase (Far Red) and imaged using ImageXpress Micro.

The results of this example show that the colonies that were generated in Example 4 display comparable colony size/morphology to colonies generated in commercially available lipid enhanced BSA.

Example 6

Figure 6:
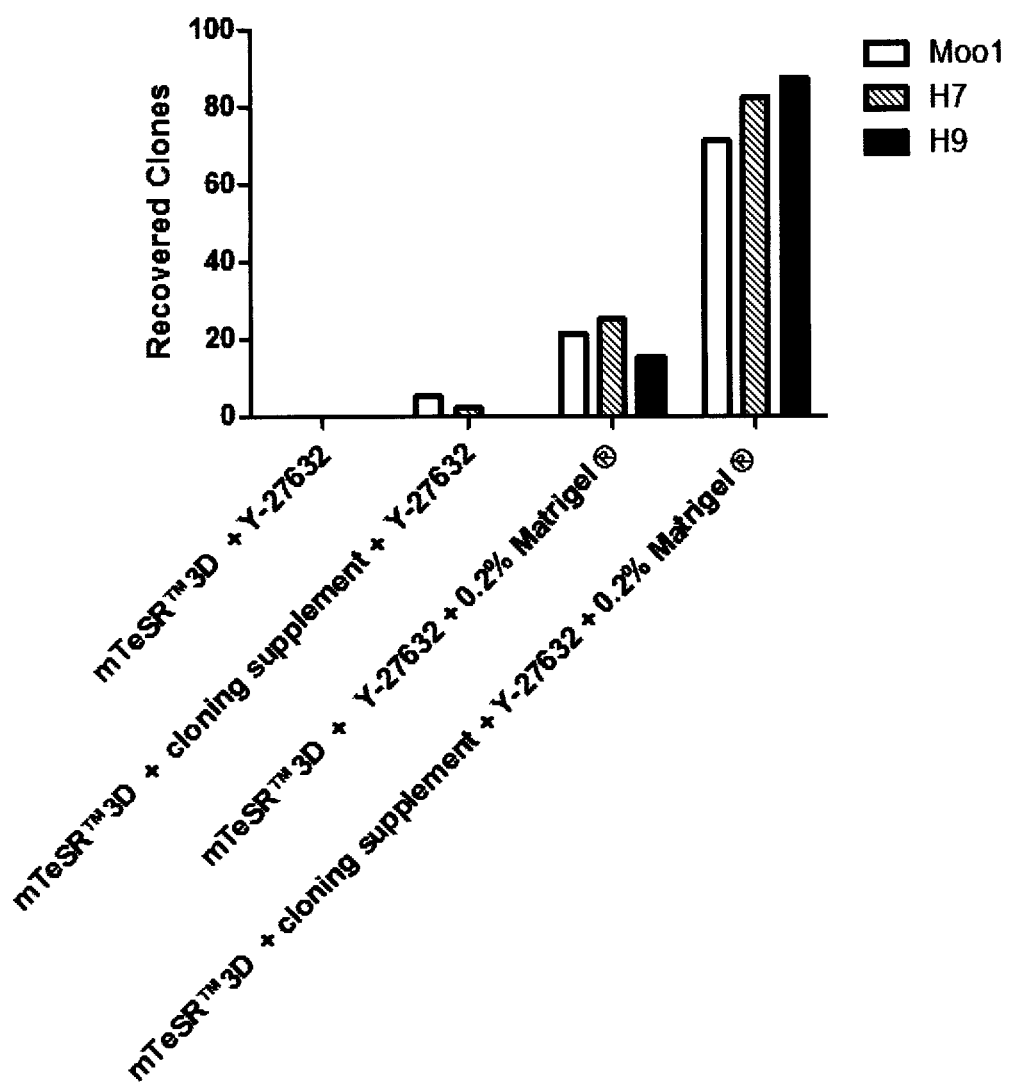
FIG. 6 is a bar graph showing the % cloning efficiency of hPSC cultured under non-adherent conditions in various culture media.

The results of this example are shown in FIG. 6 and demonstrate that STiPS-M001, H7, and H9 hPSCs cultured under non-adherent conditions in medium comprising Y-27632 and either lipid enriched albumin or 0.2% Matrigel® exhibit a higher number of recovered clones per well than when cultured with lipid enriched albumin-free media and Y-27632. These results further show that medium comprising Y-27632, lipid enriched albumin and 0.2% Matrigel® exhibit a substantial and synergistic effect, with a much higher number of recovered clones per well than would be expected by adding the recoveries observed using medium containing any single of these components.

Example 7

Figure 7:
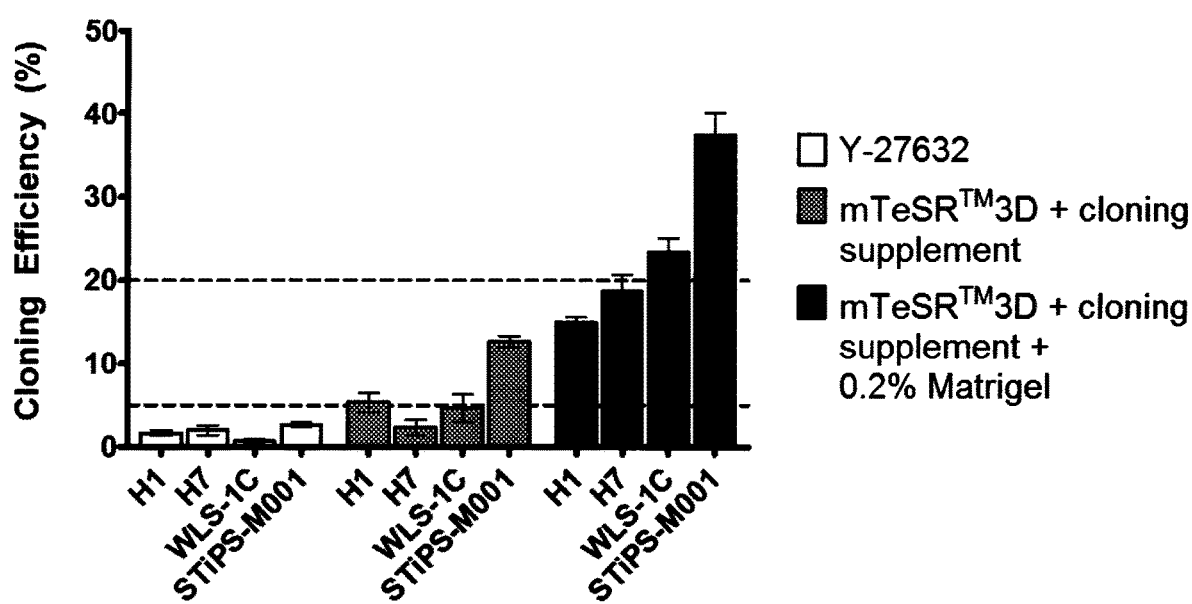
FIG. 7 is a bar graph showing the number of recovered clones of hPSC cultured under non-adherent conditions in various culture media.

The results of this example are shown in FIG. 7 and demonstrate that STiPS-M001, WLS-1C, H7, and H9 hPSCs cultured under non-adherent conditions in medium comprising Y-27632 and either lipid enriched albumin or lipid enriched albumin and 0.2% Matrigel® exhibit a higher cloning efficiency (number of clones recovered divided by number of cells seeded) per well than when cultured with lipid enriched albumin-free media and Y-27632.

Example 8

Figure 8:
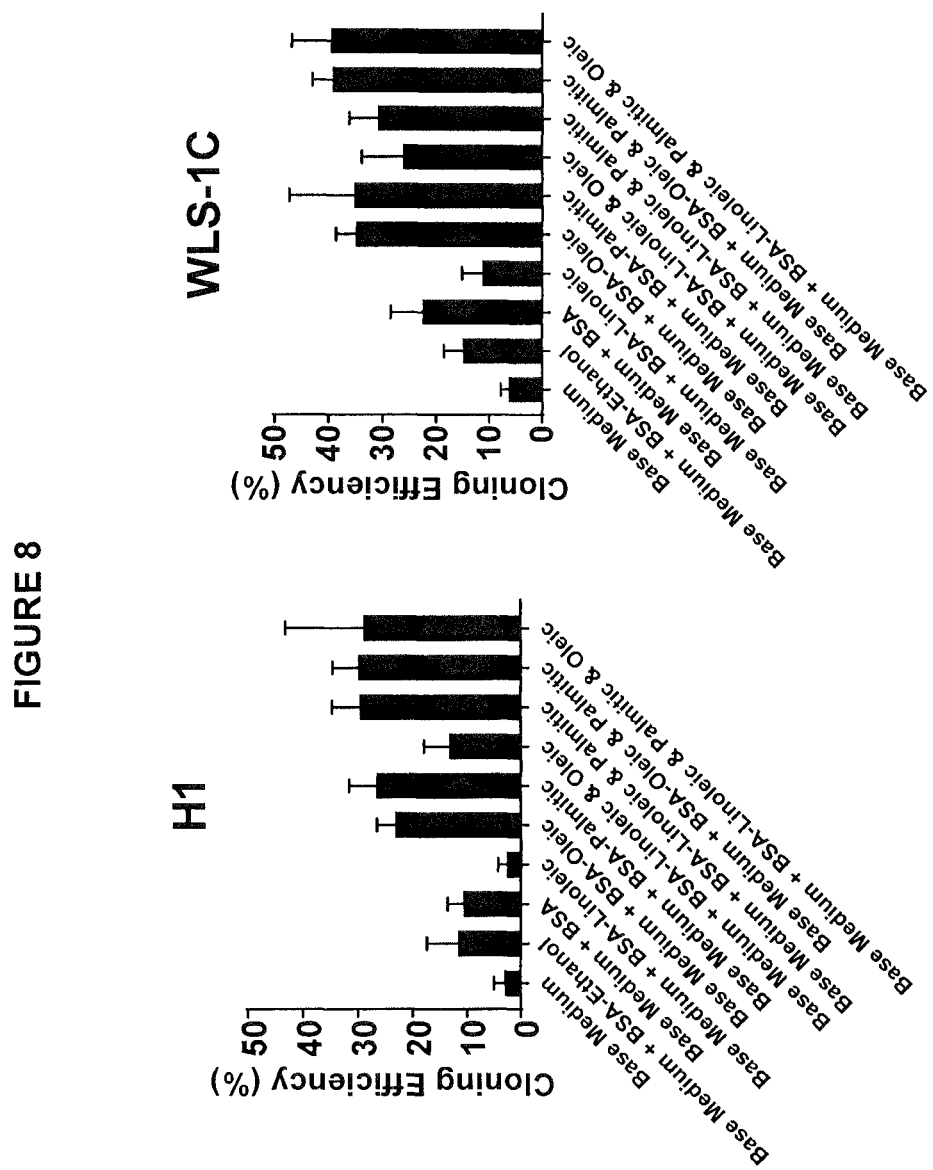
FIG. 8 is a bar graph showing that lipid-loading different fatty acids individually or in combination onto a low-lipid BSA increases cloning efficiency.

The results of this example are shown in FIG. 8 and demonstrate that WLS-1C, H1 and STiPS-F016 cells cultured in the presence of an otherwise lipid poor albumin (ie. substantially free of lipid) that has been loaded with a single fatty acid, two fatty acids or three fatty acids exhibit varying levels of cloning efficiency depending on the nature of the one or two fatty acids.

In particular, each of the one or more fatty acids was incubated with albumin at a concentration of 600 µg of each fatty acid per gram of albumin. The product of such incubation was subsequently added to the culture medium at a final concentration of 6 ng/m L.

H1, WLS-1C, and STiPS-F016 hPSCs displayed comparable cloning efficiencies when treated with either oleic acid or palmitic acid, or both, in comparison to the 3 fatty acid-loaded albumin (as shown in FIG. 8).

Notably, loading only linoleic acid may reduce cloning efficiency in WLS-1C and H1 hPSCs below the levels of control and both oleic acid and/or palmitic acid.

Example 9

Figure 9:
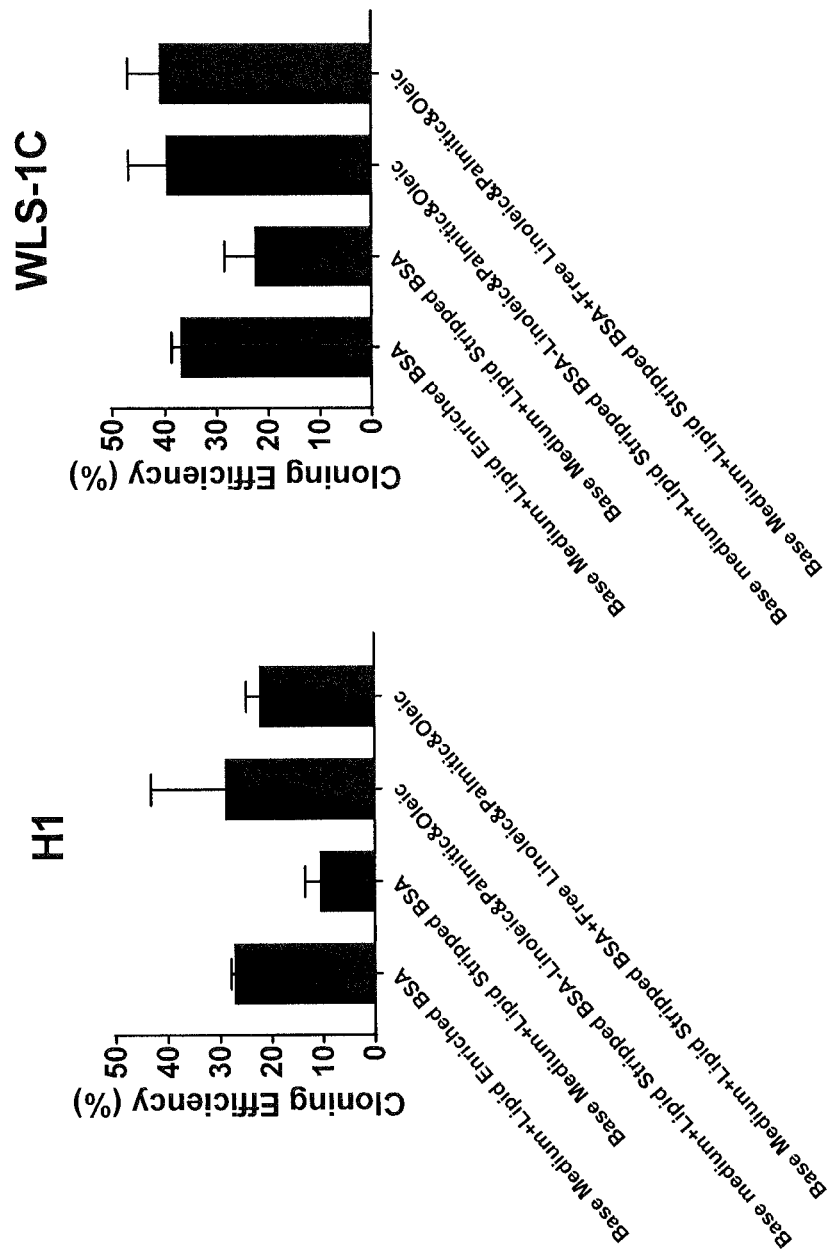
FIG. 9 is a bar graph showing that adding lipids in the presence of a carrier increases cloning efficiency and does not have to be specifically lipid-loaded.

The results of this example are shown in FIG. 9 and demonstrate that cloning efficiency may be enhanced by adding free fatty acid to a medium comprising additional low-lipid (ie. lipid-free or lipid-reduced) carrier.

WLS-1C, H1 and STiPS-F016 cells cultured in the presence of either three free fatty acids (palmitic, oleic, and linoleic) plus carrier or an albumin loaded with three fatty acids (palmitic, oleic, and linoleic) exhibit comparable levels of cloning efficiency.

In particular, 600 μg of each fatty acid per gram of albumin was incubated to yield the lipid-enriched albumin. Or, 600 μg of each free fatty acid per gram of additional low-lipid albumin were spiked into the cell culture. After 4 days of culture under these conditions (with a medium change at day 2) followed by 7 days of culture in standard mTeSR™ 1 the cloning efficiency of each cell line in each culture condition was assessed.

It is notable that providing the three free fatty acids without additional low-lipid carrier may also yield appreciable cloning efficiency levels.

Example 10

Figure 10A:
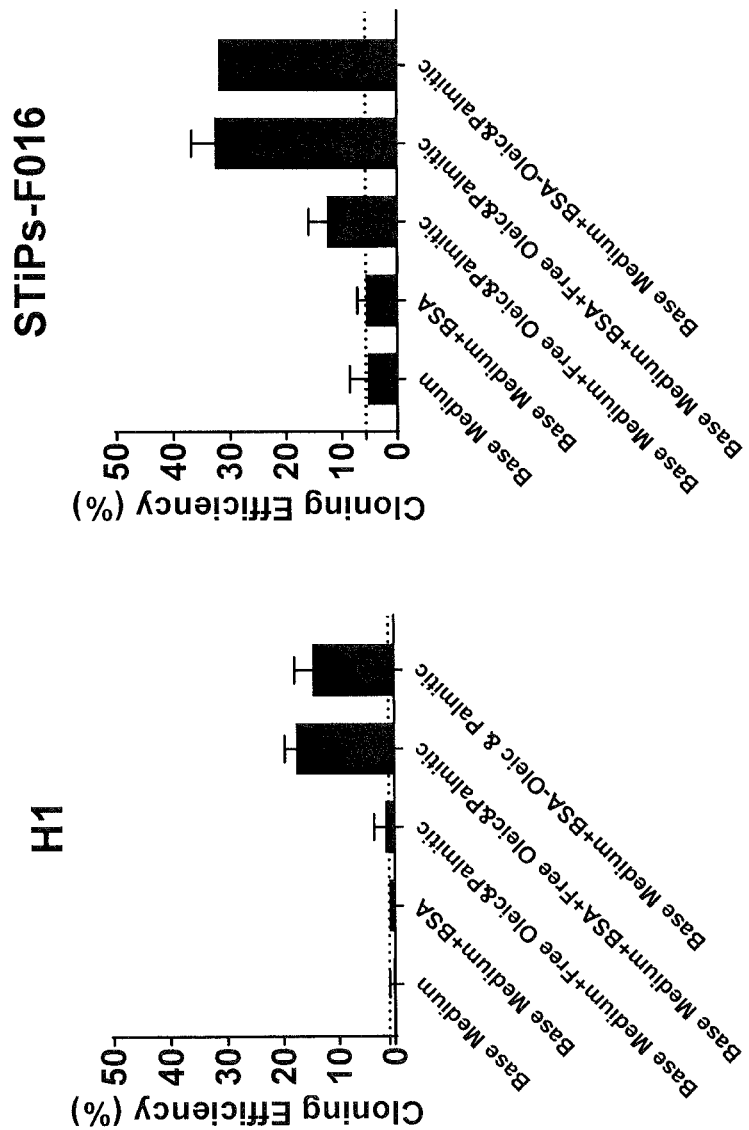
FIG. 10 is a bar graph showing
Figure 10B:
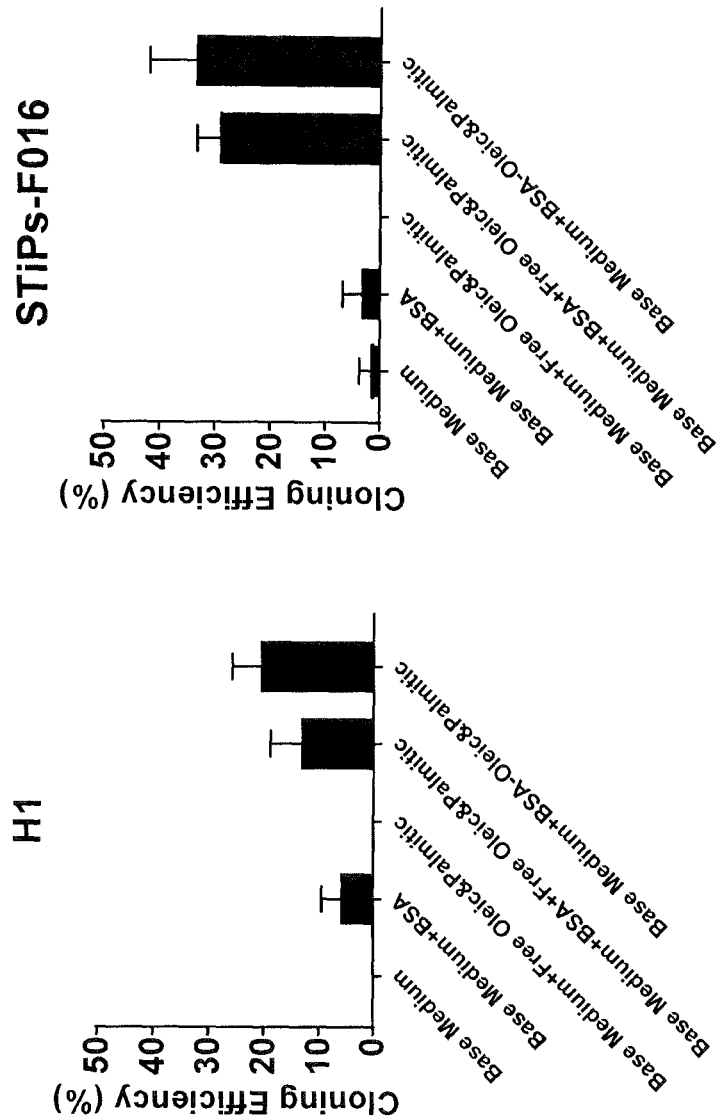

The results of this example are shown in FIG. 10 and demonstrate that, whether in mTeSR™1 (FIG. 10a) or in TeSR™E8™ (FIG. 10b), spiking free fatty acids achieves better cloning efficiency for H1, 1C and STiPS-F016 hPSCs when the free fatty acids are provided in the presence of additional low-lipid carrier.

Specifically, when using a protein-reduced medium, such as TeSR™E8™, the inclusion of additional carrier is necessary to enhance the cloning efficiency of cells exposed to free fatty acids.

Example 11

Figure 11:
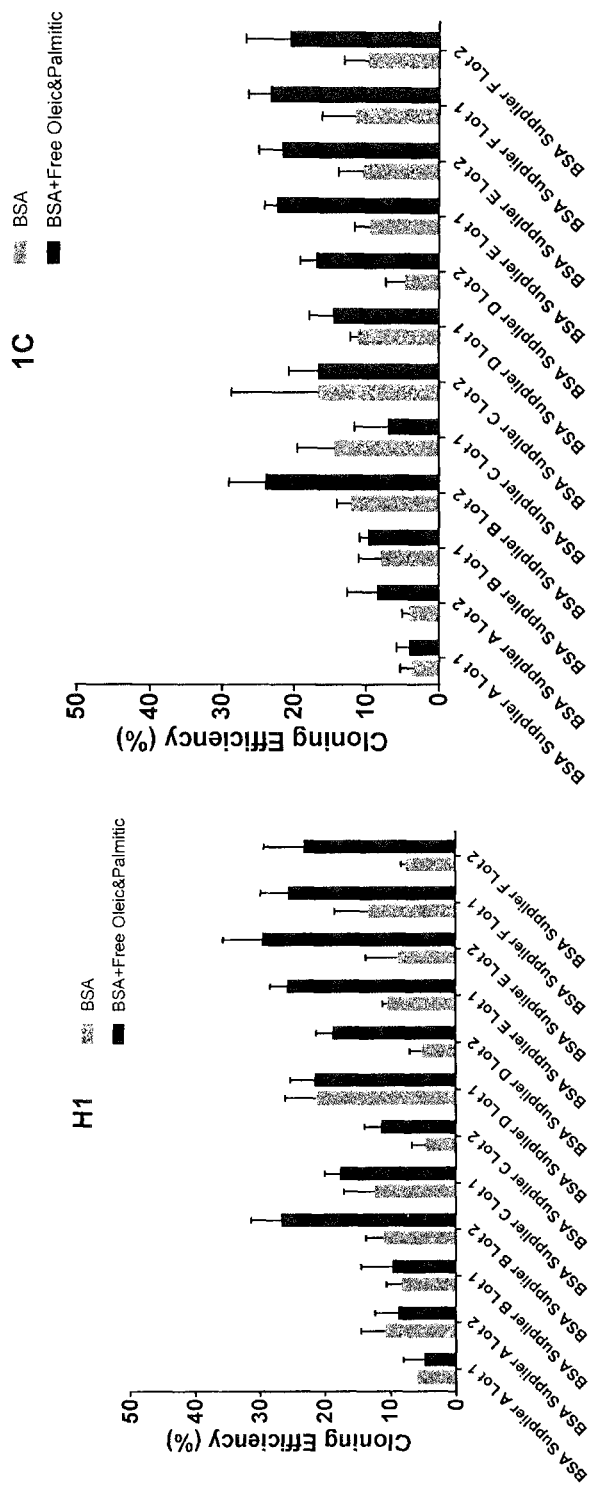
FIG. 11 is a bar graph showing that the cloning efficiency of media comprising BSA from multiple BSA suppliers can be improved by adding free fatty acids. Supplier A lot 1&2, Supplier B lot 1 and Supplier C lot 1 BSAs already comprise of 3000-7000 ug/g of overall fatty acid. Rest of the suppliers BSAs contain less than 400 ug/g overall fatty acid.

The results of this example are shown in FIG. 11 and demonstrate that the cloning efficiencies of WLS-1C and H1 cells using two different albumins or albumin lots from 4 different suppliers are enhanced when providing said albumins along with two free fatty acids to the culture of cells.

Notably, the cloning efficiencies using an albumin from one supplier (A1 and A2) were not enhanced when providing said albumins along with two free fatty acids. Of further note, albumins A1 and A2 yielded the lowest cloning efficiencies even without the presence of the additional two free fatty acids. This observation may arise due to the high overall levels of many fatty acids and/or the presence of one or more fatty acids detrimental to cloning efficiencies.

Example 12

Figure 12:
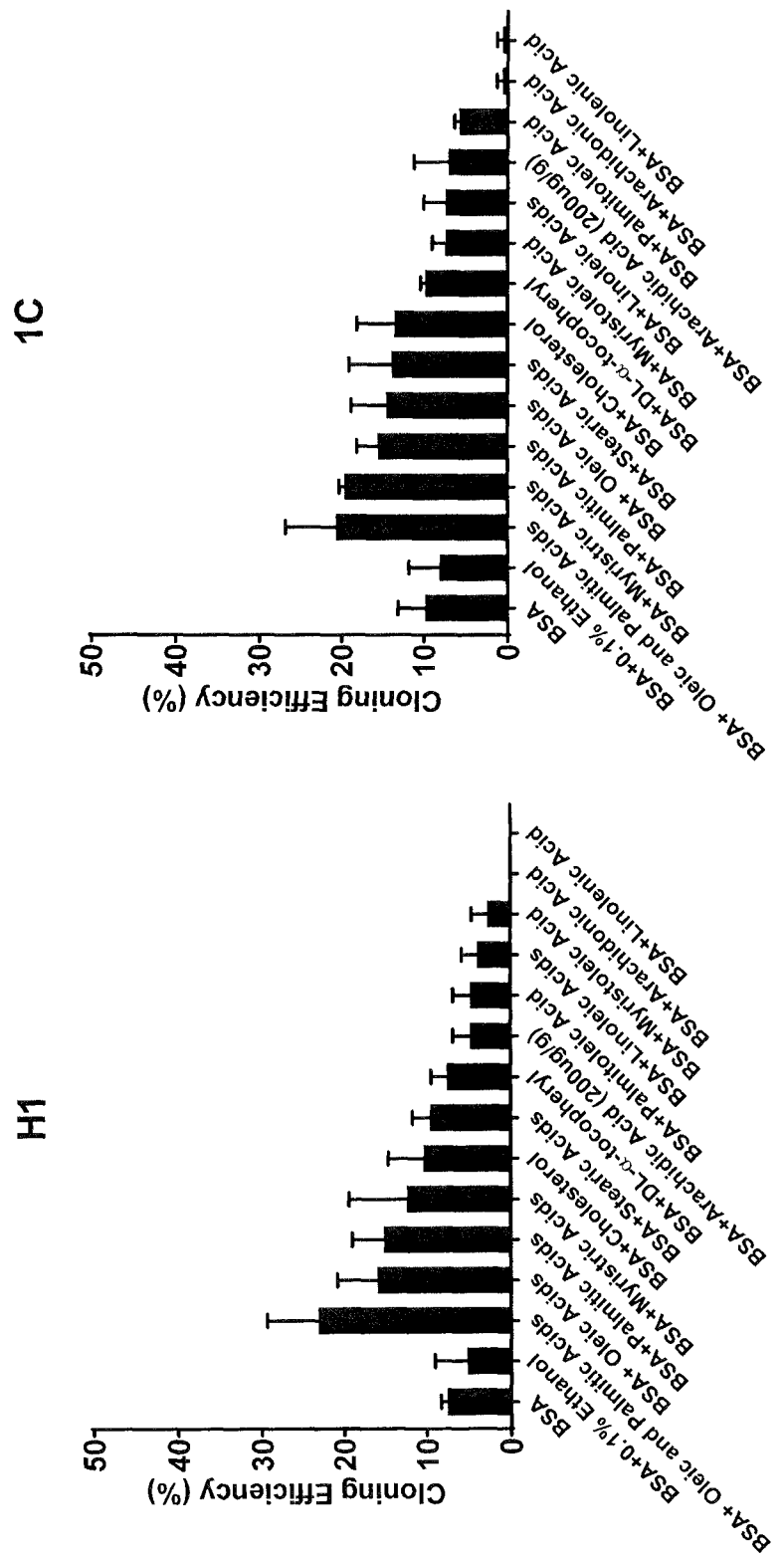
FIG. 12 is a bar graph showing that fatty acids have different effects on cloning efficiency, some are beneficial whereas others are detrimental.

The results of this example are shown in FIG. 12 and demonstrate the effect of individual free fatty acids in the presence of a carrier on the cloning efficiencies of H1 and WLS-1C hPSCs.

In this experiment, 600 μg of the shown free fatty acids were spiked into culture medium (mTeSR™1 plus 10 μM Y-27632) per gram of carrier also spiked into the culture medium. Cloning efficiencies were calculated as described in Example 1, for example.

Whereas at least oleic acid, palmitic acid, myristic acid, stearic acid and cholesterol may be helpful in enhancing the survival and proliferation of H1 and WLS-1C hPSCs, it appears that the presence of at least arachidonic acid and α-linolenic acids may be detrimental.

Example 13

Figure 13:
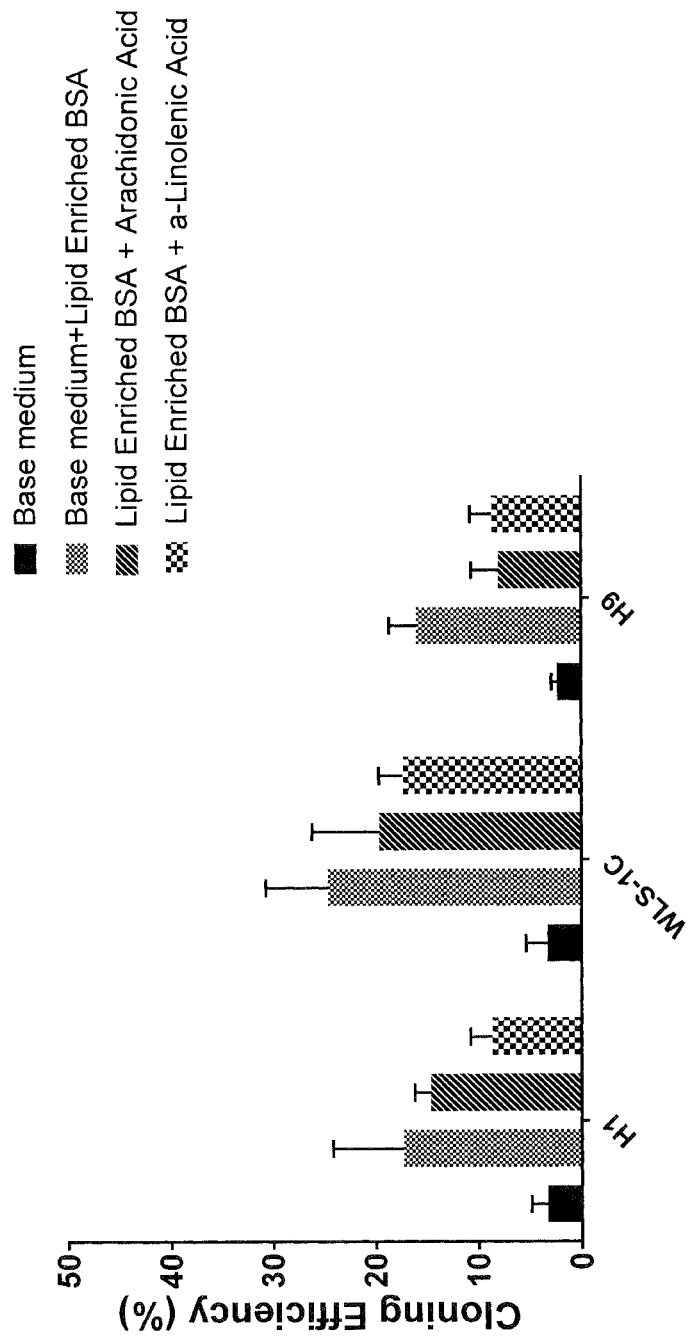
FIG. 13 is a bar graph showing that adding detrimental fatty acids to a lipid enriched BSA has a negative effect on cloning efficiency.

The results of this example are shown in FIG. 13 and demonstrate that loading a carrier with certain fatty acids is detrimental to cloning efficiencies of cells exposed thereto.

In the experiment shown in FIG. 13, 300 μg/g of either arachidonic acid or α-linolenic acid were loaded onto a specific BSA sample and added to a culture comprising H1, WLS-1C, and H9 hPSCs. Each of the loaded fatty acids decreased the cloning efficiency of the tested BSA sample.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

The invention claimed is:

1. A cloning supplement comprising one or more small molecule inhibitors and two or more lipids in the presence of a carrier, wherein
   the carrier is an agent, substance, composition or complex that transports some or all of the two or more lipids to a mammalian pluripotent stem cell,
   the two or more lipids comprise oleic acid and palmitic acid,
   the amount of each alpha-linolenic acid and/or arachidonic acid is less than 300 μg per gram of carrier, and
   wherein the survival or proliferation of mammalian pluripotent stem cells is enhanced in a culture medium containing the supplement as compared to a culture medium that does not contain the supplement.

2. The cloning supplement according to claim 1, further comprising one or more of Mead's acid, arachidic acid, palmitoleic acid, myristic acid, myristoleic acid, linoleic acid, stearic acid, alpha-linolenic acid, arachidonic acid, cholesterol, and DL-alpha-tocopheryl.

3. The cloning supplement according to claim 1, wherein the cloning efficiency is 5% to 65%.

4. The cloning supplement according to claim 1, wherein the pluripotent stem cells are ES cells or iPS cells.

5. The cloning supplement according to claim 1, wherein the carrier is an agent for transporting the one or more lipids to the one or more mammalian pluripotent stem cells.

6. The cloning supplement according to claim 1, wherein the carrier is an albumin, a liposome, an extracellular vesicle, an exosome, a nanostructured lipid carrier, or a cyclodextrin.

7. The cloning supplement according to claim 6, wherein the albumin is human.

8. The cloning supplement according to claim 6, wherein the albumin is recombinant.

9. The cloning supplement according to claim 1, wherein at least some of the one or more lipids are bound to the carrier.

10. The cloning supplement according to claim 1, wherein a concentration of the one or more lipids ranges from 1 ng/ml to 35 μg/ml.

11. The cloning supplement according to claim 1, wherein the cloning supplement is diluted in the mammalian pluripotent stem cell culture medium.

12. The cloning supplement according to claim 1, wherein the one or more small molecule inhibitors is Thiazovivin, Y-27632, CHIR99021, S8202190, MI-7, Necrostatin-1, NS3694, Wnt-C59, NSCI, or BIPV5.

* * * * *